US006755789B2

(12) United States Patent
Stringer et al.

(10) Patent No.: US 6,755,789 B2
(45) Date of Patent: Jun. 29, 2004

(54) ULTRASONIC VASCULAR IMAGING SYSTEM AND METHOD OF BLOOD VESSEL CANNULATION

(75) Inventors: Bradley J. Stringer, Farmington, UT (US); Gary A. Simmons, Farmington, UT (US); Douglas A. Christensen, Salt Lake City, UT (US); Shayne Messerly, Farmington, UT (US); Cameron P. Ford, Kaysville, UT (US); Robert W. Evensen, Layton, UT (US)

(73) Assignee: Inceptio Medical Technologies, LLC, Farmington, UT (US)

( * ) Notice: Subject to any disclaimer, the term of this patent is extended or adjusted under 35 U.S.C. 154(b) by 88 days.

(21) Appl. No.: 10/072,662

(22) Filed: Feb. 5, 2002

(65) Prior Publication Data

US 2003/0149366 A1 Aug. 7, 2003

(51) Int. Cl.[7] .................................................. A61B 8/14
(52) U.S. Cl. ...................................... 600/461; 600/441
(58) Field of Search ................................. 600/407, 437, 600/438, 440, 441, 442, 443, 447, 449–472; 128/916; 73/595–633; 367/7, 11, 130, 138

(56) References Cited

U.S. PATENT DOCUMENTS

| | | |
|---|---|---|
| 3,556,079 A | 1/1971 | Omizo |
| 3,777,740 A | 12/1973 | Hokanson |
| 3,888,238 A | 6/1975 | Meindl et al. |
| 4,143,650 A | 3/1979 | Hatke |
| 4,373,533 A | 2/1983 | Iinuma |
| 4,402,324 A | 9/1983 | Lindgren et al. |
| 4,408,692 A | 10/1983 | Sigel et al. |
| 4,475,553 A | 10/1984 | Yamaguchi et al. |
| 4,593,699 A | 6/1986 | Poncy et al. |
| 4,622,978 A | 11/1986 | Matsuo et al. |
| 4,646,722 A | 3/1987 | Silverstein et al. |

(List continued on next page.)

FOREIGN PATENT DOCUMENTS

| | | |
|---|---|---|
| EP | 0 341 718 A1 | 11/1989 |
| EP | 0 376 396 A2 | 7/1990 |
| EP | 0 467 291 A1 | 1/1992 |
| EP | 0 477 581 A1 | 4/1992 |

OTHER PUBLICATIONS

Scott, D.H.T., "Editorial II, 'In the Country of the Blind, the One–eyed Man is King', Erasmus (1466–1536)," British Journal of Anaesthesia 82 (6): pps. 820–1, 1999.

"Ultrasound Technologies," www.ultrasound.demon.co.uk/Company.html, ©2002, (3 pages), Ultrasound Technologies Ltd.

"Bard, Site–Rite Ultrasound System," wwwdymax–usa-.com, ©2001, (8 pages), Dymax Corporation.

(List continued on next page.)

Primary Examiner—Ali M Imam
(74) Attorney, Agent, or Firm—TraskBritt

(57) ABSTRACT

An apparatus, method and system for cannulation of blood vessels. The apparatus comprises a sensor assembly including two linear transducer arrays oriented perpendicularly to each other to form a "T" shape to provide substantially simultaneous ultrasound images of at least one blood vessel in a portion of a patient's body in two perpendicular planes. The apparatus may also include one or more Doppler transducer elements to transmit and receive one or more Doppler beams at an incident angle beneath one of the transducer arrays and in alignment therewith to determine blood flow direction and velocity within the at least one blood vessel. The sensor assembly may be disposed within an elongated, flexible, protective sheath and secured to a graphically marked cover to facilitate orientation of the sensor assembly on the patient and guidance of a needle towards a desired target vessel during the cannulation procedure. The cover may also include associated structure to cooperate with a reference location element to place, align and secure the sensor assembly to the patient's skin at a desired location.

36 Claims, 12 Drawing Sheets

U.S. PATENT DOCUMENTS

| | | | |
|---|---|---|---|
| 4,794,933 A | 1/1989 | Yamazaki |
| 4,887,606 A | 12/1989 | Yock et al. |
| 5,080,103 A | 1/1992 | Olivier |
| 5,136,825 A | 8/1992 | White, Jr. |
| 5,167,629 A | 12/1992 | Vertenstein et al. |
| 5,168,863 A | 12/1992 | Kurtzer |
| 5,220,923 A | 6/1993 | Hagiwara et al. |
| 5,259,383 A | 11/1993 | Holstein et al. |
| 5,259,386 A | 11/1993 | Sharkawy |
| 5,261,407 A | 11/1993 | Nishigaki et al. |
| 5,311,871 A | 5/1994 | Yock |
| 5,351,698 A | 10/1994 | Wheeler et al. |
| 5,363,852 A | 11/1994 | Sharkawy |
| 5,394,877 A | 3/1995 | Orr et al. |
| 5,427,108 A | 6/1995 | Bollinger |
| 5,490,522 A | 2/1996 | Dardel |
| 5,520,657 A | 5/1996 | Sellers et al. |
| 5,779,625 A | 7/1998 | Suzuki et al. |
| 5,891,039 A | 4/1999 | Bonnefous et al. |
| 5,910,113 A | 6/1999 | Pruter |
| 5,957,850 A | 9/1999 | Marian, Jr. et al. |
| 6,014,473 A | 1/2000 | Hossack et al. |
| 6,117,152 A | 9/2000 | Huitema |
| 6,132,379 A | 10/2000 | Patacsil et al. |
| 6,224,543 B1 | 5/2001 | Gammons et al. |
| 6,261,234 B1 | 7/2001 | Lin |
| 6,293,907 B1 | 9/2001 | Axon et al. |
| 6,293,914 B1 | 9/2001 | Sumanaweera et al. |
| 6,423,002 B1 | 7/2002 | Hossack |

OTHER PUBLICATIONS

"Aspen Ultrasound System, Imagegate Release," www.acuson.com/aspen/home_aspen_rad.html, ©2002, (4 pages), Acuson, A Siemens Company.

"The ACUSON Sequoia® 512 ultrasound platform ushers in a new era for diagnostic ultrasound," www.acuson.com/sequoia/sequoia_gi_home.html, ©2002, (3 pages), Acuson, A Siemens Company.

"Toshiba, Medical Systems," http://medical.toshiba.com/clinical/cardiology/nemio153.html, ©2002, (2 pages), Toshiba.

Hatfield et al., "Clinical Investigations, Portable ultrasound for difficult central venous access," British Journal of Anaesthesia 82 (6): pps. 822–6, 1999.

Partial International Search, dated Jul. 22, 2003.

PCT International Search Report, dated Nov. 21, 2003.

AHRQ (Agency for Health Care Research and Quality) Study, Making Health Care Safer, A Critical Analysis of Patient Safety Practices, Evidence Report/Technology Assessment, No. 43, (no date), 11 pages.

Albin, M.S. "Air Emboloism." Embolism II, I I, Mar. 1, 1999, 1–24.

Alderson, P.J., Burrows, F.A. "The Use of Ultrasound to Facilitate Central Venous Cannulation in Young Children." Anesthesiolgy, 77, 3A, Sep. 1992, A1196.

Andrews, R.T., Bova, D.A., Venbrux, A.C. "How much Guidewire is too much? Direct Measurement of the Distance from Subclavian and Internal Jugular Vein Access Sites to the Superior Vena Cava–Atrial Junction During Central Venous Catheter Placement." Critical Care Medicine, 2000, 28, 1, 138–142.

Andrews, T.A., Osterman, F.A. "Technical Note: Antegrade Access to the Superficial Femoral Artery Using a Dedicated Vascular Access Ultrasound Device." Applied Radiology, Aug. 1998, 33–36.

Aoki, H., Mizobe, T., Nozuchi, S., et al. "Vertebral Artery Pseudoaneurysm: A Rare Complication for Internal Jugular Vein Catheterization." Anesth Analg, 1992, 75, 296–298.

Applebaum, R.M., Adelman, M.A., Kanschuger, M.S., Jacobowitz, G., Kronzon, I. "Transesophageal Echocardiographic Identification of a Retrograde Dissection of the Ascending Aorta Caused by Inadvertent Cannulation of the Common Carotid Artery." Journal of the American Society of Echocardiography, 10, 7, Sep. 1997, 749–751.

Arditis, J., Giala, M., Anagnostidou, A. "Accidental Puncture of the Right Lymphatic Duct During Pulmonary Artery Catheterization. A Case Report." Acta Anaesthesiologica Scandinavica, 1988, 32, 67–68.

Armstrong, P.J., Sutherland, R., Scott, D.H.T. "The Effect of Position and Different Maneuvers on Internal Jugular Vein Diameter Size." Acta Anaesthesiologica Scandinavica, 1994, 38, 229–231.

Armstrong, P.J. Cullen, M., Scott, D.H.T., "The 'SiteRite' Ultrasound Machine—An Aid to Internal Jugular Vein Cannulation," Anaesthesia, 1993, vol. 48, pp. 319–323.

Arnold, S., Feathers, R.S., Gibbs, E. "Bilateral Pneumothraces and Subcutaneous Emphysema: A Complication of Internal Jugular Venepuncture." British Medical Journal, 1973, 1, 211–212.

Asheim, P. Aadahl, P. Fasting, S. "[Ultrasound Guidance for Placement of Central Venous Catheters]." Tidsskr Nor Loegeforen, 24, 1999, 119, 3605–3606.

Bailey, A.R. "A Close Shave: Air Embolism Following Laceration of Central Venous Catheter." Anaesthesia, 51, Mar. 1996, 294.

Bazaral, M., Harlan, S. "Ultrasonic Anatomy of the Internal Jugular Vein Relevant to Percutaneous Cannulation." Critical Care Medicine, Apr. 1981, 9, 4, 307–310.

Blank, R., Rupprecht, H.J., Schorrlepp, M., Kopp, H., Rahmani, R. "[Clinical Importance of Ultrasonic Sound Guided Puncture of Femoral Vessels with Smart Needle in Cardiac Catheterization]." Zeitschrift fuer Kardiologie, 86, 8, 1997, 608–614.

Brass, P., Volk, O., Leben, J., Schregel, W. "[Central Venous Cannulation –Always with Ultrasound Suport?]." Anaesthesiol Intensivmed Notfallmed Schmerzther, 2001, 36, 619–627.

Burns, S., Herbison, G.J. "Spinal Accessory Nerve Injury as a Complication of Internal Jugular Vein Cannulation." Annals of Internal Medicine, Oct. 15, 1996, 125, 8, 700.

Caridi, J.G., Hawkins, I.F., et al., "Sonographic Guidance when Using the Right Internal Jugular Vein for Central Vein Access." AJR, 171, Nov. 1998, 1259–1263.

Colley, D.P. "Vertebral Arteriovenous Fistula: An Unusual Complication of Swan–Ganz Catheter Insertion." AJNR, Jan/Feb 6, 1985, 103–104.

Conz, P.A., Dissegna, D., Rodighiero, M.P., LaGreca, G. "Cannulation of the Internal Jugular Vein: Comparison of the Classic Seldinger Technique and an Ultrasound Guided Method." Journal of Nephrology, 10, 6, 1997, 311–313.

Damen, J., Bolten, D. "A Prospective Analysis of 1400 Pulmonary Artery Catheterizations in Patients Undergoing Cardiac Surgery." Acta Anaesthesiologica Scandinavica, 1986, 30, 386–392.

Davies, M.J., Cronin, K.D., Comaingue, C.M. "Pulmonary Artery Catheterisation: An Assessment of Risks and Benefits on 220 Surgical Patients." Anaesthesia and Intensive Care, X, 1, Feb. 1982, 9–14.

Denys, B.G., Uretsky, B.F., Reddy, P.S. "Ultrasound–Assisted Cannulation of the Internally Jugular Vein. A Prospective Comparison to the External Landmark–Guided Technique." Circulation, 87, 5, May 1993, 1557–1562.

Depierraz, B., Essinger, A., Morin, D., Goy, J.J., Buchser, E. "Isolated Phrenic Nerve Injury After Apparently Atraumatic Puncture of the Internal Jugular Vein." Intensive Care Medicine, 1989, 15, 132–134.

Doblar, D.D., Hinkle, J.C., Fay, M.L., Condon, B.F. "Air Embolism Associated with Pulmonary Artery Catheter Introducer Kit." Anesthesiology, 56, 307–309. 1982.

Downie, A.C., Reidy, J.F., Adam, A.N. "Short Communication: Tunneled Central Venous Catheter Insertion via the Internal Jugular Vein Using a Dedicated Portable Ultrasound Device." British Journal of Radiology, Feb. 1996, 69, 818, 178–181.

Eckhardt, W.F., Iaconetti, D.J. Kwon, J.S., et al. "Inadvertent Carotid Artery Cannulation During Pulmonary Artery Catheter Insertion." Journal of Cardiothoracic and Vascular Anesthesia, 10, 2 (Feb.), 1996, 283–290.

Ellerbrock, U. "[Neurological Complications in Connection with the Placing of a Catheter Into the Internal Jugular Vein]." Anaesthesist, 1984, 33, 121–122.

Farrell, J., Gellens, M. "Ultrasound Guided Cannulation versus the Landmark–Guided Technique for Acute Haemodialysis Access." Nephrology Dialysis Transplantation, 1997, 12, 1234–1237.

Ferrall, H. "US–Guided Puncture of the Internal Jugular Vein: An Unexpected Anatomic Relationship." JVIR, 9, 5, Sep–Oct 1998, 854–855.

Fleischer, F., Fleischer, E., Krier, C. "[The Internal Jugular Vein Catheter—Success and Complication and its Relation to Experience]." Anaesthesiol Intensivmed Notfallmed Schmerzther, 22, 1987, 94–98.

Fry, W.R., Clagett, G.C., O''Rourke, P.T. "Ultrasound–Guided Central Venous Access." Arch. Surg., 134, Jul. 1999, 738–741.

Gilbert, T.B., Seneff, M.G., Becker, R.B. "Facilitation of Internal Jugular Venous Cannulation Using an Audio–Guided Doppler Ultrasound Vascular Access Device: Results From a Prospective, Dual–Center, Randomized, Crossoverd Clinical Study." Critical Care Medicine, 23, 1, Jan. 1995, 60–65.

Gobeil, F., Couture, P., Girard, D., Plante, R. "Carotid Artery–Internal Jugular Fistula: Another Complication Following Pulmonary Artery Catheterization Via the Internal Jugular Venous Route." Anesthesiology, 80, 1, Jan 1994, 230–232.

Golden, L.R. "Incidence and Management of Large–Bore Introducer Sheath Puncture of the Carotid Artery." Journal of Cardiothoracic and Vascular Anethesia, 9, 4 (Aug.), 1995, 425–428.

Gordon, A.C., Saliken, J.C., et al. "US–Guided Puncture of the Internal Jugular Vein: Complications and Anatomic Considerations." JVIR, 1998, 9, 2 (Mar.–Apr.), 333–338.

Gratz, I., Afshar, M., et al. "Doppler–Guided Cannulation of the Internal Jugular Vein: A Prospective, Randomized Trial." Journal of Clinical Monitoring, 10, 3, May 1994, 185–188.

Guezeldemir, M.E., Uestuensoez, B. "Ultrasonographic Guidance in Placing a Catheter for Continuous Auxiliary Brachial Plexus Block." Anesth Analg, 1995, 81, 882–883.

Haro, M., Izquierdo, M., et al. "[Diaphragm Paralysis as a Complication of Puncture of the Internal Jugular Vein]." Archivos de Bronconeumologia, 32, 2, 1996, 105–107.

Hastings, G.S., et al., "Compulsory Use of Site–Rite Sonographic Guidance for Low Internal Jugular Vein Access Eliminates Major Puncture–Related Complications," No. 68, p. S90 (date unknown).

Hatfield, A. and Bodenham, A. "Portable Ultrasound for Difficult Central Venous Access." British Journal of Anaesthesia, 82, 6, 822–826 (1999).

Hayashi, Y. "A Lethal Complication of Internal Jugular Vein Catheterization." Anesth Analg, 1993, 76, 910.

Hayashi, Y., Uchida, O., Takaki, O., et al. "Internal Jugular Vein Catheterization in Infants Undergoing Cardiovascular Surgery: An Analysis of the Factors Influencing Successful Catheterization." Anesth Analg, 1992, 74, 688–693.

Heatly, T., et al., "Comparison of the Conventional Landmark Technique and an Ultrasound–Guided Approach for the Placement of Central Venous Indwelling Catheters," p. A333 (date unknown).

Ho, A.M.–H., Chung, D.C., Tay, B.A., Yu, L.M., Yeo, P. "Diluted Venous Blood Appears Arterial: Implications for Central Venous Cannulation." Anesth Analg, 2000, 91, 1356–1357.

Hrics, P., Wilber, S., Blanda, M.P., Gallo, U. "Ultrasound–Assisted Internal Jugular Vein Catheterization in the ED." American Journal of Emergency Medicine, 16, 4, Jul. 1998, 401–403.

Hudson, P.A., Rose, J.S. "Real–time Ultrasound Guided Internal Jugular Vein Catheterization in the Emergency Department." American Journal of Emergency Medicine, 15, 1, Jan. 1997, 79–82.

Hullander, M., Spillane, W., Leivers, D., Balsara, Z. "The Use of Doppler Ultrasound to Assist with Sciatic Nerve Blocks." Regional Anesthesia, 1991, 16, 282–284.

Irita, K., et al., "Tension Hemothorax Causred by Inadvertent Insertion of an Introducer/Dilator Into the Vertebral Artery," Letters to the Editor, pp. 241–242 (date unknown).

Iserson, K.V., Copeland, J. "Pulmonary and Aortic Punctures—Complications of an Attempt at Internal Jugular Venipuncture." Journal of Emergency Medicine, 1984, 1, 227–231.

Jain, U., Shah, K.B., Belusko, R.J., et al., "Subclavian Artery Laceration and Acute Hemothorax on Attempted Internal Jugular Vein Cannulation." Journal of Cardiothoracic and Vascular Anesthesia, 5, 6 (Dec.), 1991, 608–610.

Jarosz, J.M., McKeown, B., Reidy, J.F., "Short–term Femoral Nerve Complications Following Percutaneous Transfemoral Procedures." JVIR, May–Jun. 1995, 6, 351–353.

Kayashima, K., et al., "A Reliable Method for Internal Jugular Vein Catheterization for Neonates and Infants Using a Small–Caliber Doppler Probe," Dept. of Anesthesia, Kyushu–Koseinenkin Hospital, Kitakyushu, 806, 1996, pp. 1424–1429.

Kihara, S, et al., "Central Venous Access Via the Distal Femoral Vein Using Ultrasound–Guidance," Dept. of Anesthesiology and Institute of Clinical Medicine, Univ. of Tsukuba, Tsukuba, 305–8575, Dept. of Anesthesiology and Intensive Care, Hamamatsu Univ. School of Medicine, Hamamatsu, 431–3124, 1998, pp. 1253–1257.

Knoblanche, G.E. "Respiratory Obstruction Due to Haematoma Following Internal Jugular Vein Cannulation." Anaesthesia and Intensive Care, VII, 3, Aug. 1979, 286.

Kocis, K.C., Vermillion, R.P., Callow, L.B., et al. "Complications of Femoral Artery Cannulation for Perioperative Monitoring in Children." The Journal of Thoracic and Cardiovascular Surgery, 112, 5, 1399–1400.

Konichezky, S., Saguib, S., Soroker, D. "Tracheal Puncture. A Complication of Percutaneous Internal Jugular Vein Cannulation." Anaesthesia, 1983, 38, 572–574.

Kua, J.S.W., Tan, I.K.S. "Airway Obstruction Following Internal Jugular Vein Cannulation." Anaesthesia, 1997, 52, 776–785.

Kuebler, A., Golebiowska, B., Plawiak, T. "[Ultrasound Guided Cannulation of Internal Jugular Vein]." Przeglad Lekarski, 1997, 54, 11, 802–805.

Kwon, T.H., Kim, Y.L., Cho, D.K. "Ultrasound–Guided Cannulation of the Femoral Vein for Acute Haemodialysis Access." Nephrology Dialysis Transplantation, 1997, 12, 1009–1012.

La Grange, P. du P., Foster, P.A., Pretorius, L.K. "Application of the Doppler Ultrasound Bloodflow Detector in Supraclavicular Brachial Plexus Block." British Journal of Anaesthesia, 1978, 50, 965–967.

Lampmann, L.E.H., Schuur, K.H. "Utilization of Ultrasound Guidance in Difficult Femoral Artery Puncture." European Journal of Radiology, 18, 1994, 20–21.

Lane, P., Waldron, R.J. "Real–Time Ultrasound–Guided Central Venous Access via the Subclavian Approach." Anaesthesia and Intensive Care, 22, 6, Dec. 1995, 728–730.

Lang, S.A. "Ultrasound and the Femoral Three–in–One Nerve Block: Weak Methodology and Inappropriate Conclusions." Anesth Analg, 1998, 86, 1147–1148.

Lennon, P. "Dural Puncture as a Complication of Internal Jugular Vein Cannulation." Anesthesiology, 84, 4, Oct. 1996, 944.

Liberman, L., Hordof, A.J., Hsu, D.T., Pass, R.H. "Ultrasound–Assisted Cannulation of the Right Internal Jugular Vein During Electrophysiologic Studies in Children." Journal of Interventional Cardiac Electrophysiology, 2001, 5, 177–179.

Lichtenstein, D. Saiefi, R. "The Internal Jugular Veins are Asymmetric. Usefulness of Ultrasound Before Catheterization." Intensive Care Medicine, 2001, 27, 301–305.

Lips, U. Conrad, I., Zevounou, F. Schappler–Scheele, B. "[Report on Two Cases of Irreversible Horner''s Syndrome After Puncture of the Internal Jugular Vein]." Anaesthesiol Intensivmed Notfallmed Schmerzther, 1982, 17, 301–302.

Lobato, E.B., Sulek, C.A., Moody, R.L., Morey, T.E. "Cross–Sectional Area of the Right and Left Internal Jugular Veins." Journal of Cardiothoracic and Vascular Anesthesia, 13, 2 (Apr.), 1999, 136–138.

Macintyre, P.A., Samra, G., Hatch, D.J. "Preliminary Experience with the Doppler Ultrasound Guided Vascular Access Needle in Paediatric Patients." Paediatric Anaesthesia, 2000, 10, 361–365.

Majeski, J.A. "Vertebral Arteriovenous Fistula as a Result of Swan–Ganz Catheter Insertion: Surgical Correction in a Symptomatic Patient." Int Surg, 1999, 84, 74–77.

Mallory, D.L., McGee, W.T., et al. "Ultrasound Guidance Improves the Success Rate of Internal Jugular Vein Cannulation. A Prospective, Randomized Trial." Chest, 98, 1, Jul. 1990, 157–160.

Marhofer, P., Schroegendorfer, K., et al. "Ultrasonographic Guidance Improves Sensory Block and Onset Time of Three–in–One Blocks." Anesth Analg, 1997, 85, 854–857.

Mbamalu, D., et al., "Methods of Obtaining Peripheral Venous Access in Difficult Situations," Classic Techniques in Medicine, Mar. 1999, pp. 159–162.

McGee, D.C., et al., "Preventing Complications of Central Venous Catheterization," New England Jour. Of Medicine (on–line), vol. 348, No. 12, pp. 1123–1133, Mar. 20, 2003.

McNulty, S.E., "Ultrasound–Assisted Central Venous Cannulation: Resident Teaching Tool or Practice Standard?," American Jour. Of Anesthesiology, Sep. 2000, pp. 388–389.

Mennim, P., Coyle, C.F., Taylor, J.D. "Venous Air Embolism Associated with Removal of Central Venous Catheter." BMJ, 1992, 305, 171–172.

Miller, J.A., Singireddy, S., Maldjian, P., Baker, S.r. "A Reevaluation of the Radiographically Detectable Complications of Percutaneous Venous Access Lines Inserted by Four Subcutaneous Approaches." The American Surgeon, Feb. 1999, 65, 125–130.

Mitchell, S.E., Clark, R.A. "Complications of Central Venous Catheterization." AJR, 133, Sep. 1979, 467–476.

Moellmann, M., von Hornstein, W.F., et al. "Percutaneous Venous Cannulation and Central Venous Line Placement by Means of Ultrasonography and Ultrasonic Doppler." Acta Anaesthesiologica Belgica, 1990, 41, 345–351.

Muhm, M., Waltl, B., Sunder–Plassmann, G., Apsner, R. "Is Ultrasound Guided Cannulation of the Internal Jugular Vein Really Superior to Landmark Techniques?" Nephrology Dialysis Transplantation, 1998, 13, 522–534.

Nice (National Institute for Clinical Excellence) Study, Final Appraisal Determination: Ultrasound location devices for placing central venous catheters, Jul. 2002, 17 pages.

Paschall, R.M., Mandel, S. "Brachial Plexus Injury from Percutaneous Cannulation of the Internal Jugular Vein." Annals of Emergency Medicine, 12, 1, Jan. 1983, 58–60.

Patel, C., Laboy, V., Venus, B., Mathru, M., Wier, D. "Acute Complications of Pulmonary Artery Catheter Insertion in Critically III Patients." Critical Care Medicine, 14, 3, 195–197.

Piechowiak, H., Buechels, H., Ingrisch, H., Hess, H. "Arteriovenous Fistula of the Vertebral Artery: A Rare Complication of Percutaneous Central Vein Puncture. A Case Report." Anaesthesist, 1984, 33, 327–329.

Pierce, E.T., Hunter, J., Bode, R.H., Lewis, K.P., Satwicz, P. "Ultrasound Guidance Facilitates Cannulation of the Femoral Artery." Anesthesiology, 81, 3A, Sep. 1994, A542.

Randolph, A.G. Cook, D.J., Gonzales, C.A., Pribble, C.G. "Ultrasound Guidance for Placement of Central Venous Catheters: A Meta–Analysis of the Literature." Critical Care Medicine, 1996, 24, 12, 2053–2058.

Reed, J., Leighton, S. "Ultrasound Facilitation of Brachial Plexus Block." Anaesthesia and Intensive Care, 22, 4, Aug. 1994, 499.

Riopelle, J., "Stroke from Mistaken Carotid Puncture Promotes Interest in Neck Vein Finders," APSF Newsletter, Fall 2000, p. 41.

Riopelle, J.M., Busch, E.H., Wood, D.G., et al. "Ultrasound–Guided Internal Jugular Venous Cannulation: An Introduction for Non–Radiologists to a Technique That is Here to Stay." J La State Med Soc, 153, Feb. 2001, 142–152.

Sakai, M., et al., "A Case of Right Phrenic Nerve Paralysis as a Complication of Internal Jugular Vein Cannulation by Anterior Approach," Dept. of Anesthesiolgy, Osaka Medical College, Osaka 569, 1993, pp. 1355–1358.

Sato, S., Ueno, E., Toyooka, H. "Central Venous Access vai the Distal Femoral Vein Using Ultrasound Guidance." Anesthesiology, 88, 3, Mar. 1998, 838–839.

Scherhag, A., Klein, A., Jantzen, J.P. "[Cannulation of the Internal Jugular Vein Aided by Two Ultrasonic Methods]." Anaesthesist, 1989, 38, 633–638.

Scott, D.H.T. ""In the Country of the Blind, the One–Eyed Man is King", Erasmus (1466–1536)." British Journal of Anaesthesia, (1999) 82, 6, 820–821.

Seldinger, S.I. "Catheter Replacement of the Needle in Percutaneous Arteriography." Acta Radiologica, 39, 368–376.

Sha, K., Simokawa, M., Kawaguchi, M., et al. "Use of Transesophageal Echocardiography Probe Imaging to Guide Internal Jugular Vein Cannulation." Anesth Analg, 1998, 87, 1032–1033.

Sheild, C.F., Richardson, J.D., Buckley, C.J., Hagood, Jr., C.O. "Pseudoaneurysm of the Brachiocephalic Arteries: A Complication of Percutaneous Internal Jugular Vein Catheterization." Surgery, Aug. 1975, 78, 2, 109–194.

Shulman, M.S., Kaplan, D.B. Lee, D.L. "An Anteromedial Internal Jugular Vein Successfully Cannulated Using the Assistance of Ultrasonography." Journal of Clinical Anesthesia, 12, Feb. 2000, 83–86.

Sing, R.F., Steffe, T.J., Branas, C.C. "Fatal Venous Air Embolism after Removal of a Central Venous Catheter." JAOA, 95, 3, Mar. 1995, 204–205.

Slama, M., Novara, A., Safavian, A., et al., "Improvement of Internal Jugular Vein Cannulation Using an Ultrasound–Guided Technique." Intensive Care Medicine, 1997, 23, 916–919.

Sloan, M.A., Muelller, J.D., Adelman, L.S., Caplan, L.R. "Fatal Brainstem Stroke Following Internal Jugular Vein Catheterization." Neurology, Jul. 1991, 41, 1092–1095.

Steinsapir, E.S., Coley, B.D., Fellmeth, B.D., Roberts, A.C., Hye, R.J. "Selective Management of Iatrogenic Femoral Artery Injuries." Journal of Surgical Research, 55, 1, Jul. 1993, 109–113.

Stern, W., Sauer, W., Dauber, W. "[Complications of Central Venous Catheterization From an Anatomical Point of View] ." Acta Anat, 1990, 138, 137–143.

Sulek, C.A., et al., "Central Venous Cannulation Should be Performed Using Ultrasound Guidance," Drug & Innovations Review, vol. 1, No. 5, Oct. 2002, 4 pages.

Sylvestre, D.L., Sandson, T.A., Nachmanoff, D.B. "Transient Brachial Plexopathy as a Complication of Internal Jugular Vein Cannulation." Neurology, May 1991, 41, 760.

Timsit, J.F., Farkas, J.C., Boyer, J.M., et al. "Central Vein Catheter–Related Thrombosis in Intensive Care Patients. Incidence, Risks Factors, and Relationship With Catheter––Related Sepsis." Chest, 114, 1, Jul. 1998, 207–213.

Traber, K.B., Gilfor, J.M., Jobes, D.R. "Ultrasound–Assisted Cannulation of the Internal Jugular Vein: A Survey of Resident Use After Graduation." Anesthesiology, 81, 3A, Sep. 1994, A1250.

Troianos, C.A., Jobes, D.R., Ellison, N. "Ultrasound Guided Cannulation of the Internal Jugular Vein." Anesthesiology, 73, 3A, Sep. 1990, A451.

Trottier, S.J. Todi, S., Veremakis, C. "Validation of an Inexpensive B–Mode Ultrasound Device for Detection of Deep Vein Thrombosis." Chest, 110, 6, Dec. 1996, 1547–1550.

Turnage, W.S., Harper, J.V. "Venous Air Embolism Occurring After Removal of a Central Venous Catheter." Anesth Analg., 1991, 72, 559–560.

Tyden, H. "Cannulation of the Internal Jugular Vein—500 Cases." Acta Anaesthesiologica Scandinavica, 1982, 26, 485–488.

Verghese, S., McGill, W.A., Patel, R., et al. "Approaches to Internal Jugular Vein Cannulation in Infants: Seeing, Hearing vs. Feeling." Anesth Analg, 1995, 80, S525.

Verghese, S., McGill, W.A. Patel, R., et al. "Internal Jugular Vein Cannulation in I nfants: Palpation vs. Imaging." Anesthesiology, 85, 3A, Sep. 1996, A1078.

Verghese, S.T., McGill, W.A., Patel, R.I., et al. "Ultrasound–Guided Internal Jugular Venous Cannulation in Infants. A Prospective Comparison with the Traditional Palpation Method." Anesthesiology, 91, 1, Jul. 1999, 71–77.

Verner, L., Stuetz, B. "[Cannulation of the Internal Jugular Vein by the Technique of Seldinger in a Patient with Severe Coagulopathy. Study About a Lethal Complication]." Anaesthesist, 1983, 185–186.

Vest, J.V., Pereira, M.B., Senior, R.M. "Phrenic Nerve Injury Associated with Venipuncture of the Internal Jugular Vein." Chest, 78, 5, Nov. 1980, 777–779.

Weimann, J., Frass, M., Traindl, O., Pidlich, J., Leithner, C. "[Acute Upper Airway Obstruction by Cervical Hematoma as a Complication of Internal Jugular Vein Catheterization]/" AMA, 17/1990, 4, 77–79.

Whittet, H.B., Boscoe, M.J. "Isolated Palsy of the Hypoglossal Nerve After Central Venous Catheterisation." British Medical Journal, 288, Apr. 1984, 1042–1043.

Zaidi, N.A., Khan, M., Naqvi, H.I., Kamal, R.S. "Cerebral Infarct Following Central Venous Cannulation." Anaesthesia, 1998,53, 186–191.

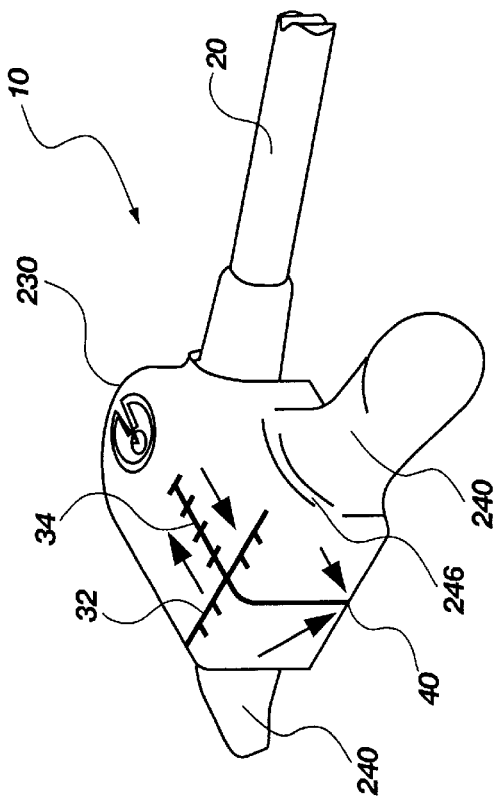
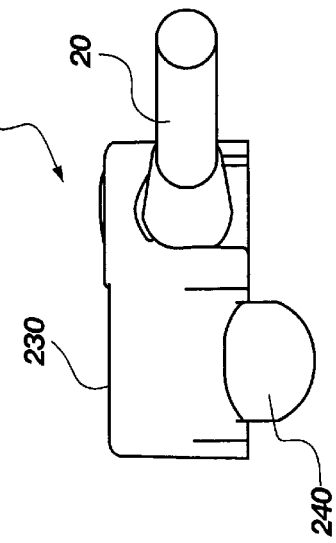
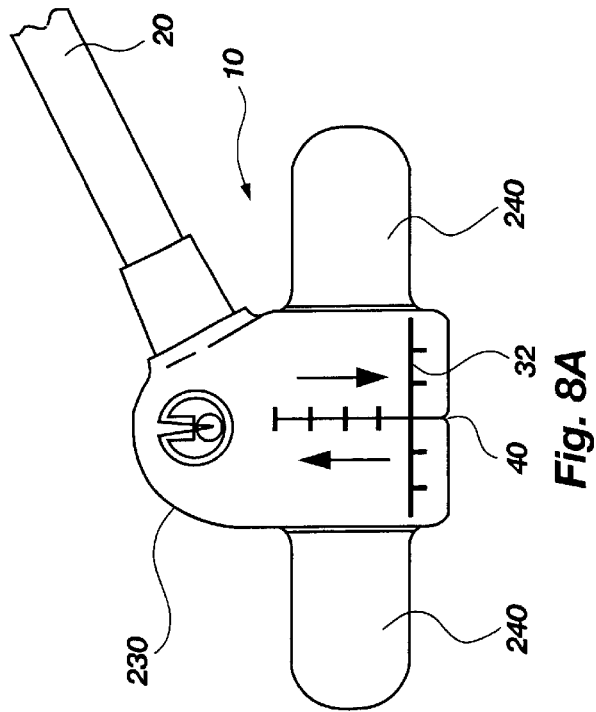
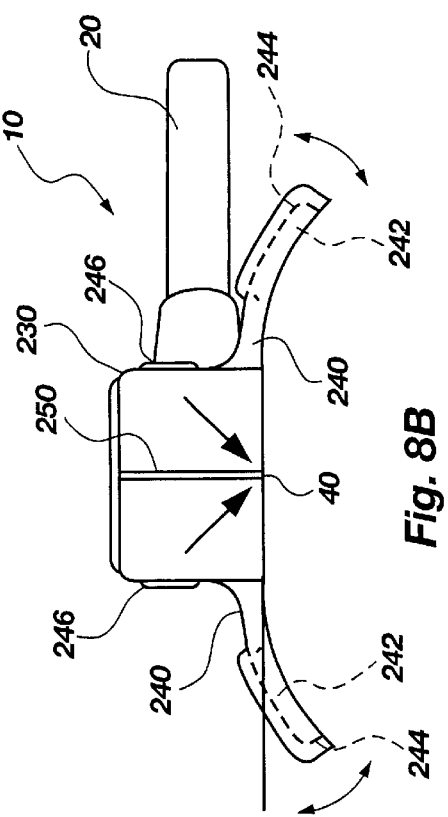

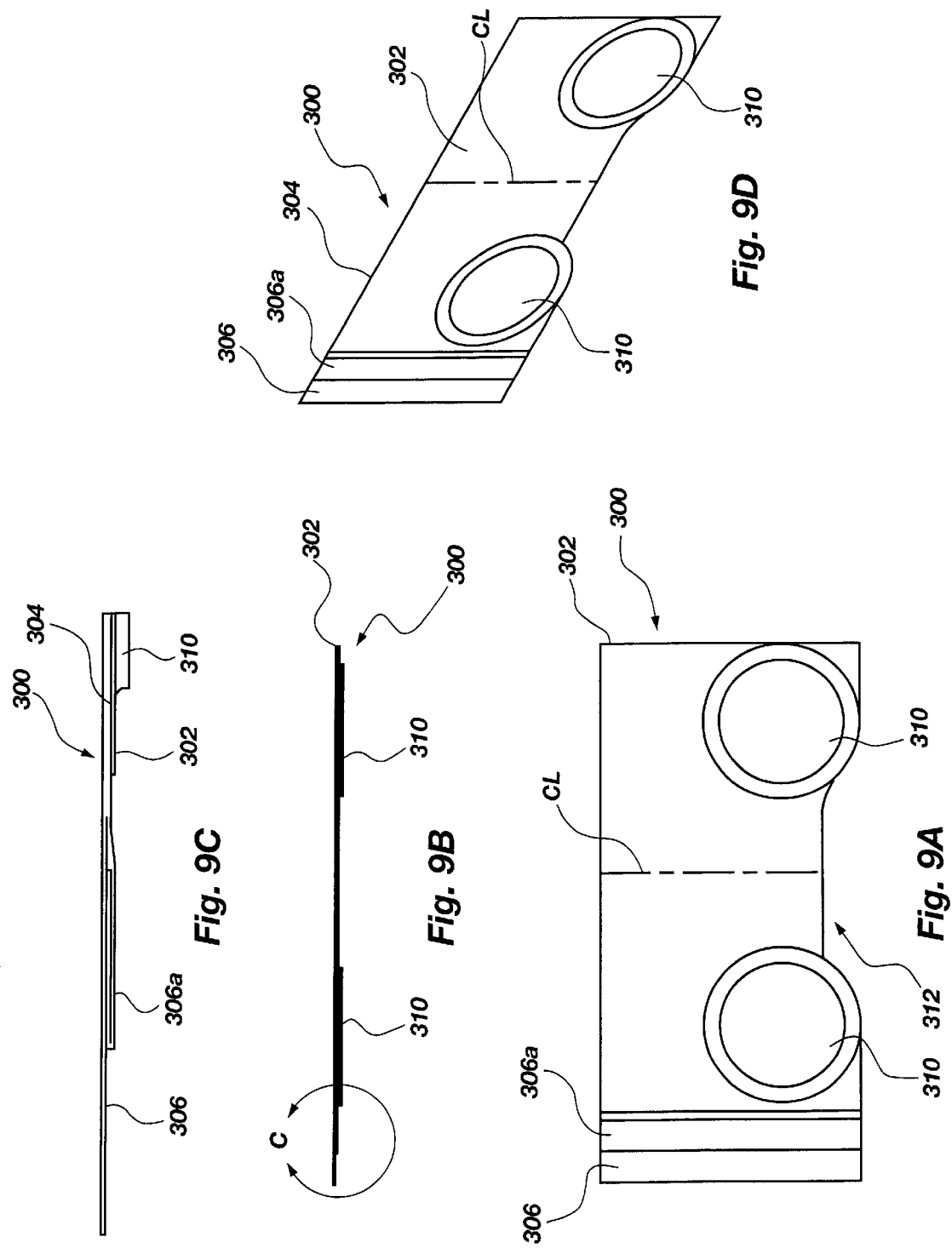

ULTRASONIC VASCULAR IMAGING SYSTEM AND METHOD OF BLOOD VESSEL CANNULATION

BACKGROUND OF THE INVENTION

1. Field of the Invention

This invention relates generally to the cannulation of veins and arteries under the guidance of ultrasound.

2. State of the Art

Insertion of catheters into central veins or arteries can be a difficult task because the vein or artery may be located deep within the body or may otherwise be difficult to access in a particular patient. Multiple attempts at penetration may result in extreme discomfort to the patient and loss of valuable time during emergency situations. Furthermore, central veins and arteries are often in close proximity to each other. While attempting to access the internal jugular vein, for example, the carotid artery may instead be punctured, resulting in severe complications or even mortality due to consequent blood loss due to the high pressure of the blood flowing in the artery.

To prevent complications during catheterization, it is known that ultrasonic instruments can be used to determine the location and direction of the vessel to be penetrated. Various approaches use a Doppler-only technique with no imaging. One such technique transmits ultrasonic waves via a transducer from the skin surface to the vessel. Due to the flow of blood in the vessel, or the pulsation of the vascular walls, the ultrasonic wave undergoes a Doppler shift effect which causes the reflected signal to be at a frequency different from the transmitted signal. The frequency difference between the transmitted and received signals is then converted to an electrical signal, amplified and sent to an audio speaker. The frequency of the tone emitted from the speaker increases as the frequency difference becomes greater, indicating the approximate location of the vessel. Improvements to this technique place either the transmitting transducer, receiving transducer, or both transmitting and receiving transducers within a hollow needle so that the audio signal becomes louder as the needle is turned towards a vessel within the patient's body. While such applications are helpful in guiding the needle towards the general location of vessels, the obtainable accuracy is obviously limited. Other limitations of this technology include difficulty distinguishing veins from nearby arteries, difficulty determining when the vessel has been penetrated, and difficulty implementing the known Seldinger technique.

Other conventional approaches to identification of vessel location and direction use two-dimensional ultrasound imaging to either mark the vessel location on the skin before attempting to access the vessel using the known Seldinger technique or view the vessel as the needle tip advances towards it. See *British Journal of Anaesthesia*, 822–6 (1999). However, it would be desirable to improve ultrasound imaging techniques for the cannulation of blood vessels to make the use of such technology less cumbersome and more accurate.

BRIEF SUMMARY OF THE INVENTION

The present invention uses ultrasound techniques in an improved method and apparatus for cannulation of blood vessels. In contrast to conventional approaches, the present invention provides a clinician with the ability to manipulate the needle during insertion with both hands while observing the progress of the needle toward and into the desired target vessel in substantially real time.

The apparatus of the invention comprises a sensor assembly including two ultrasonic, linear transducer arrays, each comprising a plurality of active imaging transducer elements, the arrays being oriented perpendicularly to each other to form a "T" configuration and carried by a housing. The 90° relative orientation of the array axes provides the ability to quickly and easily image blood vessels in both the longitudinal and transverse planes as a needle with attached catheter is guided towards a target vessel. One advantage of the present invention is that the needle operator may accurately orient the needle with respect to the target vessel and may, as desired, monitor the needle at all times as it passes through the anterior wall of the vessel. Thus, this technique and apparatus may eliminate the need to insert the first, or seeker, needle used in the Seldinger technique and greatly increase the accuracy over Doppler-only techniques where the needle operator is guided solely by an audible tone. Again, it is notable that the clinician employing the present invention is enabled to manipulate the needle during insertion with both hands while simultaneously observing the progress of the needle toward and into the desired target vessel.

In other embodiments of the present invention, the sensor assembly may be used in combination with a protective sheath having a frame element associated therewith and a cover configured to encompass the sensor assembly and bearing graphics to provide means, in cooperation with the frame element, for orienting the sensor assembly and securing the sensor assembly to the patient's body in a desired orientation.

In still another embodiment of the invention, the sensor assembly may include a housing configured to include two laterally extending protrusions or "wings" proximate the lower edges of two opposing side walls, the wings each carrying a magnet thereon. This embodiment of the sensor assembly may be employed in combination with a reference location element in the form of a dielectric (such as a polymer) film or tape bearing an adhesive on one side thereof for attachment to the skin of a patient over the general location of the blood vessel to be cannulated, the tape including two laterally spaced shims of a magnetically responsive metal or polymer. The lateral spacing of the shims approximates that of the magnets, but the shims are somewhat larger than the magnets to permit the sensor assembly to be moved about by the clinician over a limited area of the patient's body with respect to the film to precisely locate the sensor assembly. The magnets, in turn, permit such movement but exhibit magnetic fields robust enough to maintain the sensor assembly in place when it is released by the clinician.

In still a further embodiment of the invention, the housing of the sensor assembly may be configured for use with a reference location element in the form of an elongated ribbon having an adhesive coating at each end thereof, the ribbon being adhered to the skin of the patient. The ribbon extends through a slot in the sensor assembly housing, which has associated therewith at least one resilient gripping element which may be manipulated by the clinician to release tension on the ribbon to enable sliding of the sensor assembly therealong as well as limited rotation thereof with respect to the ribbon to precisely locate the sensor assembly. When a desired location of the sensor assembly is reached, then the at least one resilient gripping element is released and the sensor assembly is fixed in place.

In further embodiments of the present invention, the sensor assembly further includes at least one ultrasonic Doppler transducer element used to transmit and receive a single ultrasonic beam at an angle relative to the imaging transducer array in the longitudinal plane. The addition of the Doppler transducer element or elements provides directional blood flow and blood velocity information with regard to the target vessel and others nearby and thus improves the ability to distinguish veins from arteries. The directional information from the Doppler transducer element or elements may be converted to a color mark with one distinct color indicating blood flow in one direction and another distinct color indicating blood flow in the opposite direction. For example, when the sensor housing is appropriately aligned on the body with respect to cover markings depicting blood flow toward and away from the heart, blood flow toward the heart may be indicated with the color blue and blood flow away from the heart may be indicated with the color red. Thus, when the single color scan line is overlaid on top of a grayscale longitudinal image of a possible target vessel on a monitor screen, a blue mark on the color screen will indicate a vein and a red mark will indicate an artery. While an array of Doppler elements may also be used to provide a full-color image, a single Doppler beam reduces the complexity and cost of providing desired directional flow information.

In still another embodiment, the Doppler transducer element or elements carried by the sensor housing may be configured to transmit and receive "chirped" ultrasound pulses to obtain Doppler information at discrete depths within the body. A pulse is chirped if its carrier frequency changes with time. This frequency modulation, or frequency sweeping, causes the Fourier spectrum of the chirped pulse to broaden. Thus, a digital signal processor may be used to analyze the reflected signal via a Fast Fourier Transform ("FFT") algorithm to separate distances or depths of various features within the body. The phase change between transmitted and received signals is used to determine speed and direction of flow in the blood vessels.

In yet another embodiment, two pulsed Doppler elements may be used for determining speed and direction of flow in the blood vessels. In this embodiment, the two pulsed Doppler elements each comprise a group of active imaging transducer elements included in one of the linear ultrasonic transducer arrays, specifically the array hereinafter termed a "longitudinal" array, which is to be positioned in use over the vessels to be detected and substantially parallel thereto. The two pulsed Doppler elements, each comprising a contiguous group of active imaging transducer elements, are mutually spaced from each other along the length of the array and are each angled at the same but relatively opposing angle to a perpendicular to the plane of the array of which they are a part. The two pulsed Doppler elements each transmit and receive ultrasonic signals, by which blood flow direction and velocity may be determined.

Yet another aspect of the present invention comprises a protective sheath into which the sensor assembly may be inserted, a packaging configuration therefor and a method of use thereof. The protective sheath comprises an elongated tubular thin polymer film element, closed at one end and open at the other. The protective sheath may be tapered so as to be of larger diameter or transverse dimension at the open end than at the closed end thereof. The open end of the protective sheath is folded back over the rest of the protective sheath so that a portion comprising about one-half of the protective sheath is inside-out, or everted, and extends over the remaining portion thereof. The end of the now-everted protective sheath now open and defining a bore extending to the closed end of the sheath (the original or first open end of the protective sheath now lying adjacent and surrounding the original closed end due to eversion) is rolled outwardly back upon itself toward the closed end until only a small "pouch" or "foot" of a size suitable for receiving the sensor assembly remains, the doubled and rolled polymer film forming a toroidal shape defining a mouth of the pouch or foot. At that juncture, the skirt of material defining the now-everted original or first open end of the protective sheath is folded back over the outside of the toroidal shape of rolled polymer film. In use, the inventive protective sheath may be placed in a tray of a kit including other sterile, disposable elements of the present invention with its mouth defined by the skirt and toroidal shape of rolled polymer film facing upward. In use, the sensor assembly (which is not sterile) may be placed into the pouch or foot through the mouth and the folded-back skirt of the protective sheath grasped and pulled proximally along the cable extending to the sensor assembly to maintain sterility of the exterior of the protective sheath while encompassing the nonsterile sensor assembly and associated cable therein for use. Tabs of another material may be secured to the skirt to facilitate visual identification and grasping of the skirt.

Methods of vessel identification, a system incorporating the sensor housing of the present invention and a kit of disposable sterile components are also encompassed by the present invention.

BRIEF DESCRIPTION OF THE SEVERAL VIEWS OF THE DRAWINGS

FIGS. 8A through 8D respectively comprise a top elevation, a frontal elevation, a side elevation and a perspective view of another exemplary implementation of a sensor assembly according to the present invention for use with a magnetic reference location element;

FIGS. 9A through 9D respectively comprise a top elevation, a frontal elevation, an enlargement of a portion of the frontal elevation and a perspective view of a magnetic reference location element suitable for use with the sensor assembly embodiment of FIGS. 8A through 8D.

DETAILED DESCRIPTION OF THE INVENTION

Figure 1A:
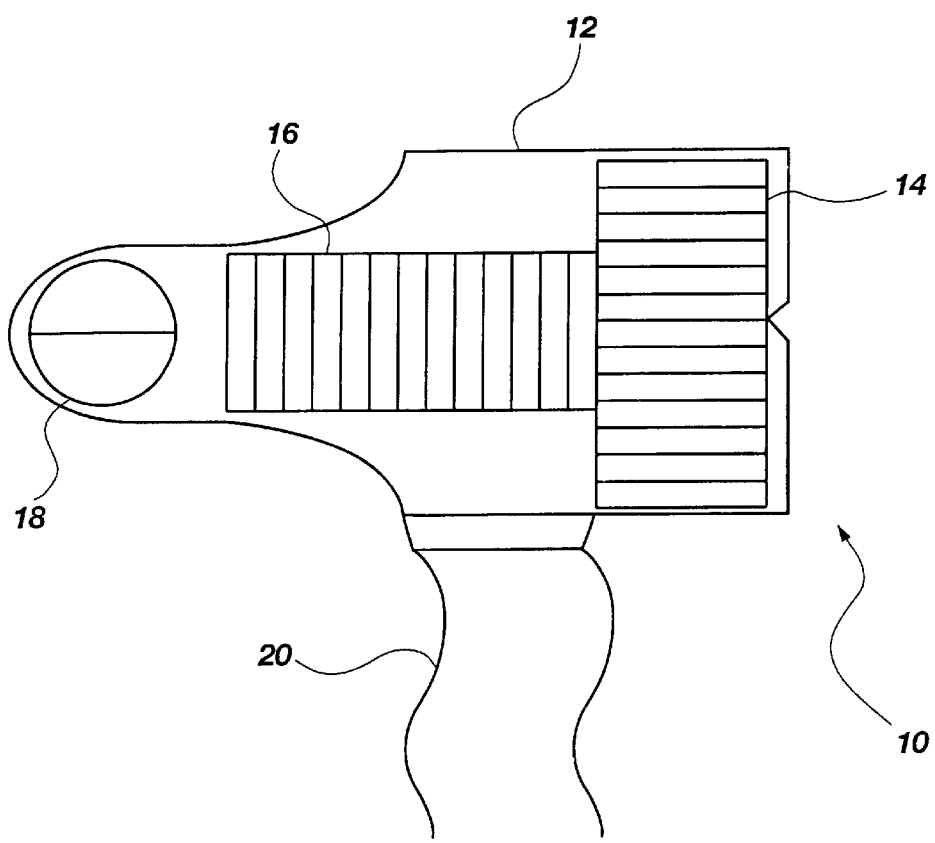
FIGS. 1A and 1B respectively comprise a bottom schematic view and a side schematic view of a first exemplary sensor assembly of the present invention.
Figure 1B:
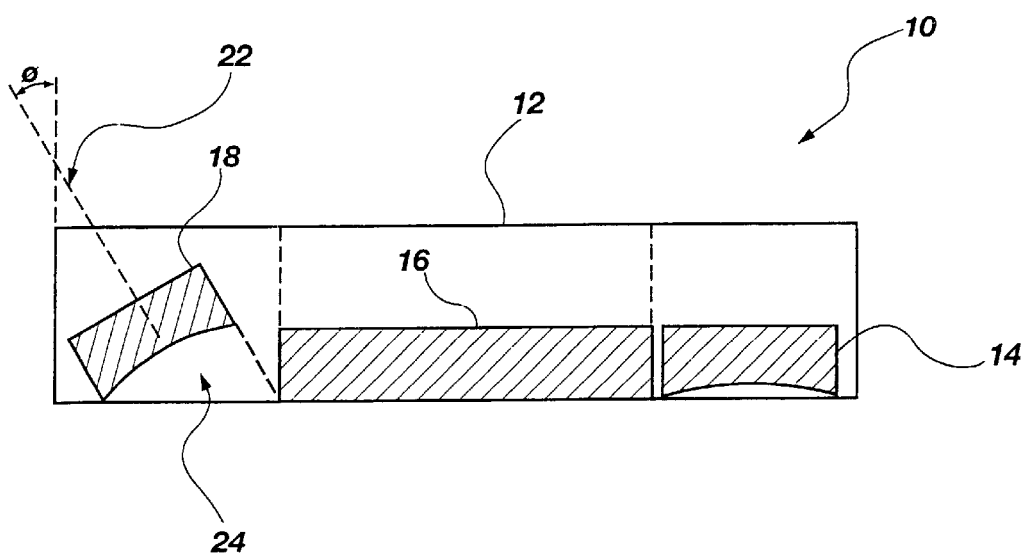

FIGS. 1A and 1B comprise a schematic illustration of a sensor assembly 10 in accordance with the present invention. The sensor assembly 10 includes a housing 12 containing a first linear, ultrasonic elongated cross-sectional or transverse transducer array 14 and a second linear, ultrasonic elongated longitudinal transducer array 16, which arrays 14 and 16 are placed perpendicular to one another. Transducer arrays 14 and 16 as assembled with housing 12 form a "T" shape and are employed to obtain ultrasonic images of potential target blood vessels simultaneously in both the transverse and longitudinal planes. Transducer array 14 defines the head of the "T," while transducer array 16 defines the body thereof. Transducer arrays 14 and 16 each extend linearly and include a plurality of mutually adjacent piezoelectric active imaging transducer elements for transmitting and receiving ultrasonic waves, as will be understood by one having skill in the field of the present invention. However, while the two linear transducer arrays 14, 16 are described and depicted as arranged in a "T" configuration, it is contemplated that any arrangement placing arrays 14, 16 in mutually perpendicular relationship is suitable and encompassed by the present invention.

In addition to transducer arrays 14 and 16, one embodiment of the apparatus of the present invention includes a "chirped" Doppler transducer element 18 for transmitting and receiving a single ultrasonic Doppler beam 22 in alignment with the longitudinal transducer array 16 and at incident angle $\phi$, for example, about 20° to about 30°, to a perpendicular to the patient's skin underlying housing 12. The Doppler transducer element 18 provides blood flow direction and velocity information as an additional feature to aid the clinician in distinguishing veins from arteries during cannulation. The Doppler transducer element 18 includes one semicircular piezoelectric transmitter Tx for generating the Doppler beam and one semicircular piezoelectric receiver Rx for receiving the reflected Doppler beam. The orientation and relative alignments of Tx and Rx may be as shown in FIG. 1A, or rotated ±90° or ±180°, as desired. Alternatively, if a "pulsed" Doppler transducer element is employed, only a single circular combination emitter and receiver element is required. Further, while Doppler transducer element 18 is shown as having a concave face in FIG. 1B, a planar or convex face is also suitable. An attached ultrasonic lens may also be employed. It will be readily recognized that while multiple transmitters and receivers may be employed to acquire Doppler information corresponding to the entire ultrasound scan and image produced by longitudinal transducer array 16, using a single beam to produce Doppler information corresponding to a single scan line traversing the target blood vessel will provide all required directional blood flow information necessary for safe vessel cannulation and at far less complexity and cost.

By way of example only, manufacturers of custom medical grade transducers such as may be suitable for use in implementing the present invention include Acoustic Imaging Transducers of Phoenix, Ariz., Krantkramer of Lewistown, Pa. and Blatek, Inc. of State College, Pa.

The sensor assembly 10 of the present invention further includes a multi-conductor cable 20 which enters housing 12 at one side thereof and is operably coupled to the cross-sectional transducer array 14, the longitudinal transducer array 16, and the Doppler transducer element 18. Also, in order to increase the efficiency of the Doppler transducer element 18 and to reduce reflections in gap area or cavity 24 created by incident angle $\phi$ of beam 22, gap area 24 may be filled with a material such as an epoxy or polymer which is substantially acoustically matched to bodily tissue. Suitable compounds include, without limitation, PMMA, PTFE, and RTV silicone available, for example and not by way of limitation, from 3M Corporation, Minneapolis, Minn. and DuPont, Wilmington, Del. Of course, gap area or cavity 24 may also be filled with an acoustic transmission gel, or be partially filled with an epoxy or polymer and partially filled with an acoustic transmission gel.

Figure 2:
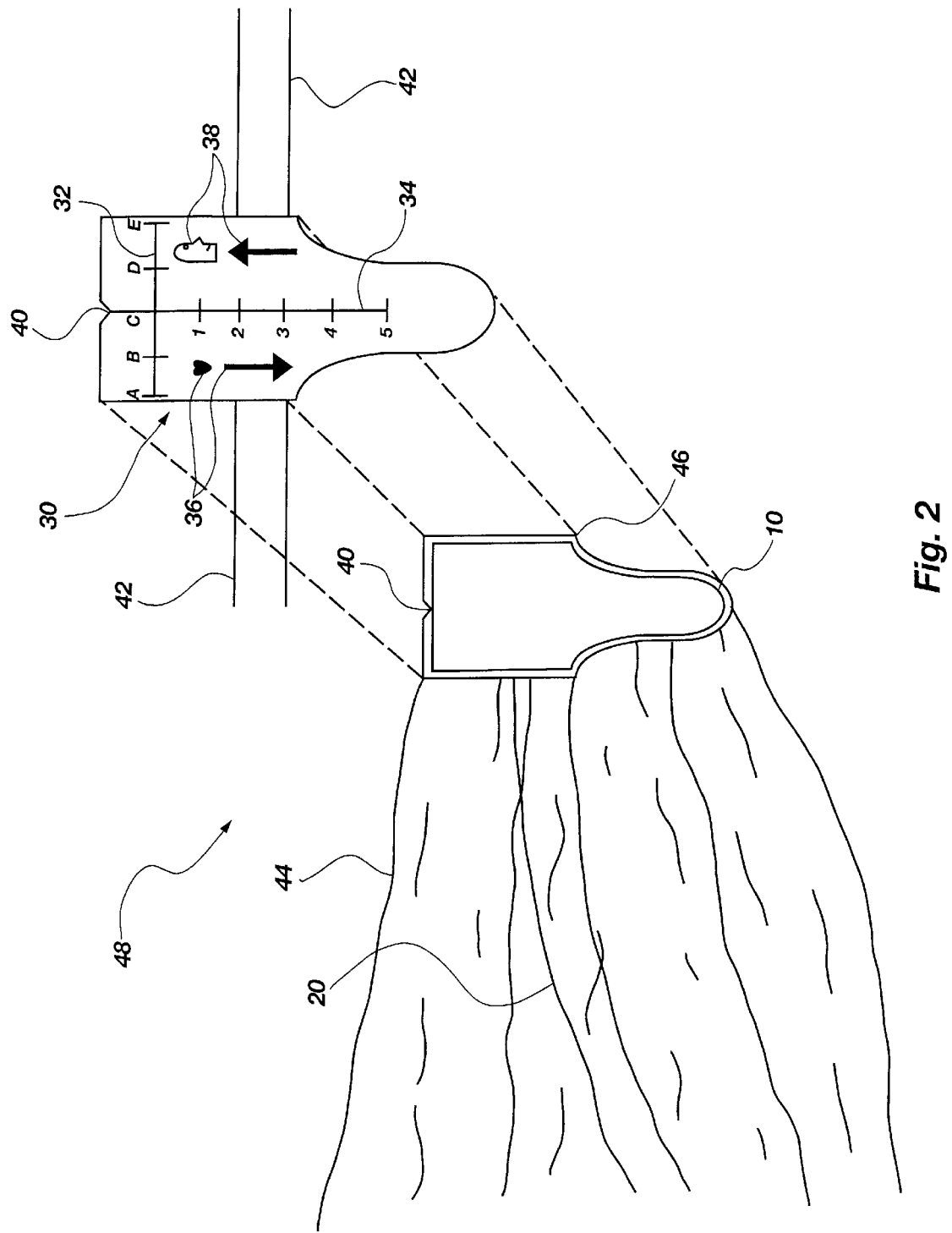
FIG. 2 is an exploded schematic view of the sensor assembly of FIGS. 1A and 1B disposed within a transparent, protective sheath and with a housing cover according to the present invention.
Figure 3:
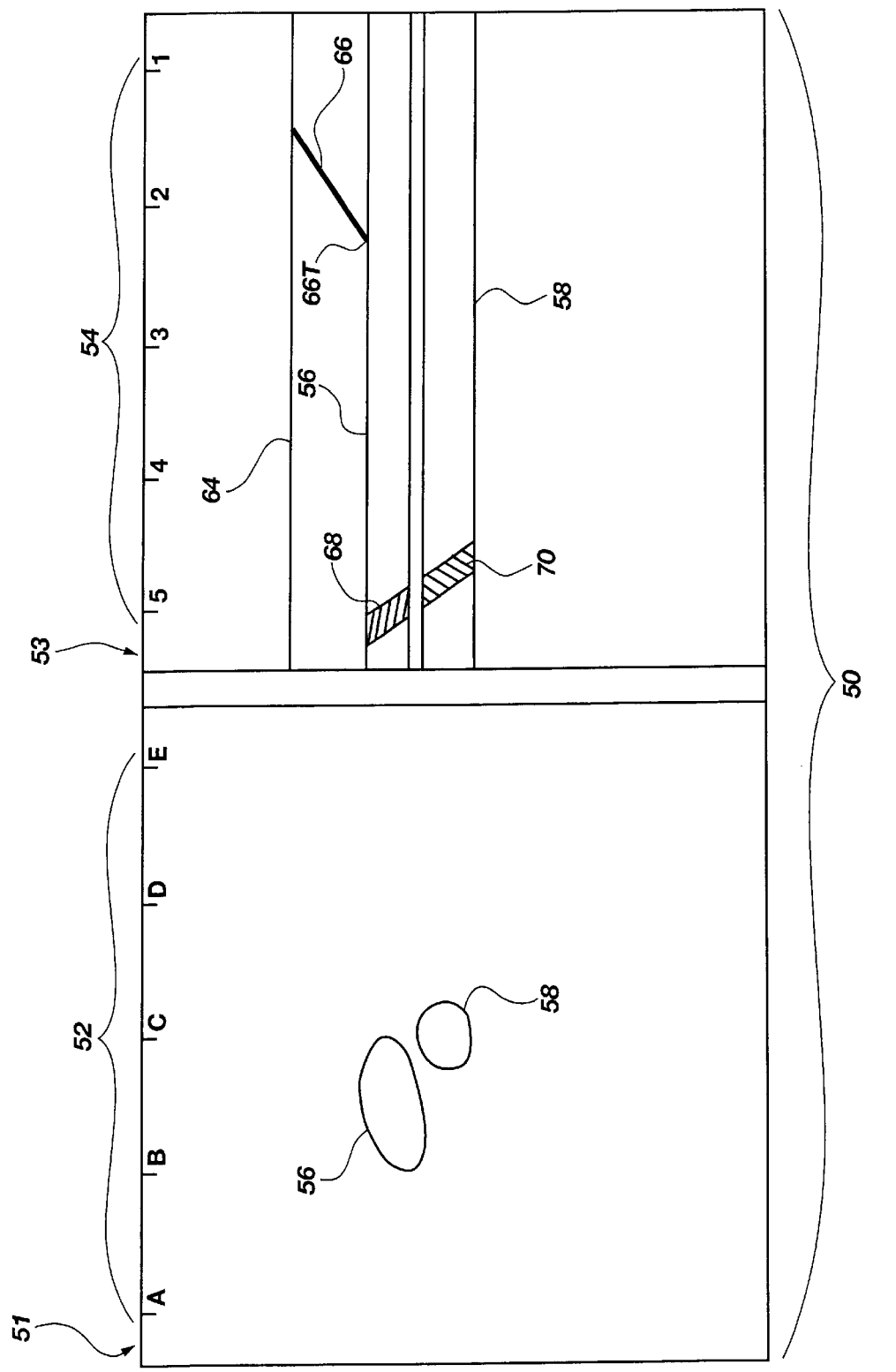
FIG. 3 comprises an exemplary dual-panel ultrasound image provided by the apparatus of the present invention of a patient's neck in two imaging planes as a needle is guided towards the internal jugular vein for cannulation.

FIG. 2 and FIG. 3 below illustrate a first, schematically illustrated, exemplary sensor assembly according to the present invention in the context of a technique for using the present invention for cannulation of the internal jugular vein located in the neck of a human patient. However, it will be apparent that the apparatus and method described may also be used to identify and access various blood vessels within a mammalian subject's body. FIG. 2 is a schematic illustration of the sensor assembly 10 as described with reference to FIGS. 1A and 1B and as viewed from above looking down on cover 30 in use with an elongated, flexible, protective and preferably transparent sheath 44 and a reference location element in the form of an elongated ribbon 42 bearing an adhesive at each end thereof to form an ultrasonic cannulation assembly 48. Cover 30 is graphically marked and configured to aid in the use of the sensor assembly 10 for the cannulation of blood vessels. The elongated, flexible, protective, transparent sheath 44 provides a protective enclosure for the sensor assembly 10 for use in a sterile field within an operating room. One suitable elongated, flexible, protective, transparent sheath for use with the present invention is offered commercially by Protek Medical Products, Inc. of Iowa City, Iowa, while another, more preferred embodiment of protective sheath 44 is described herein.

In this embodiment, the elongated, flexible, protective, transparent sheath 44 extends from a relatively larger, open end to a relative smaller, closed end to form a tapered, flaccid and thus highly flexible tubular enclosure with a frame element 46 bonded to the interior surface of the narrower, closed end thereof. The elongated, flexible, protective, transparent sheath 44, cover 30, and adhesive ribbon 42 comprise a disposable kit of sterile components for use with this embodiment of the invention and are discarded once each cannulation procedure is complete. The sensor assembly 10 may thus be reused without sterilization for new procedures with a new kit of disposable items including the protective, transparent sheath 44, cover 30, and adhesive ribbon 42.

Prior to use, conventional acoustic transmission gel is placed inside the elongated, flexible, protective, transparent sheath 44 within the area defined by the frame element 46 to provide efficient acoustic coupling between the material of the sheath 44 and the sensor assembly 10 secured to the frame element 46. After disposition of the acoustic gel, the sensor assembly 10 is inserted into the protective, transparent sheath 44 and housing 12 snapped into the frame element 46, the multi-conductor cable 20 being aligned with the longitudinal axis of the elongated, flexible, protective, transparent sheath 44 and extending to and through an opening at the opposite, wider end thereof for connection to a monitoring device. Next, the cover 30 is placed over the housing of sensor assembly 10 from the exterior of the protective, transparent sheath 44 and then engaged with the frame element 46 to tighten the cover 30 over the sensor assembly 10. After applying additional acoustic transmission gel to the patient's skin in the area to be accessed, the ultrasonic cannulation assembly 48 is placed on the patient's body in order to obtain ultrasound images of a target blood vessel.

Cover 30 bears orientation markings on its exterior surface indicating blood flow towards the heart 36 and away from the heart 38 to assist in proper orientation of sensor assembly 10 on the patient's body. For example, if attempting to cannulate the internal jugular vein of the neck, the sensor assembly 10 of the ultrasonic cannulation assembly 48 would be placed on the patient's neck with the arrow depicted in orientation marking 36 pointing towards the patient's heart and the arrow depicted in orientation marking 38 pointing towards the patient's head. Proper orientation of the ultrasonic cannulation assembly 48 ensures that information concerning blood flow direction obtained from the Doppler transducer element 18 correctly indicates whether a potential target vessel is a vein or an artery.

Cover 30 also contains slots 35 (FIG. 4) through which the adhesive ribbon 42 may pass to secure the ultrasonic cannulation assembly 48 to the skin of the patient for hands-free operation thereof during the cannulation procedure. The adhesive ribbon 42 contains an area of adhesive material on the bottom (skin contact) side toward each end thereof, leaving the center region of the adhesive ribbon 42 free of adhesive material where it comes into contact with the ultrasonic cannulation assembly 48. A suitable adhesive is a 1526 tape adhesive offered by 3M Corporation, Minneapolis, Minn. Thus, after orienting the ultrasonic cannulation assembly 48 on the patient's body and obtaining an ultrasound image of the vessel to be accessed (see FIG. 3), the adhesive ribbon 42 is adhered to the skin at both sides of sensor assembly 10. Further, the cover 30 contains resilient, movable gripping elements such as portions of a compressible spring clip (not shown in FIG. 2) extending about the sides thereof to grip the adhesive ribbon 42 when engaged therewith and create tension on both ends of the adhesive ribbon 42 to hold the ultrasonic cannulation assembly 48 tightly against the skin. Further, by disengaging the gripping elements, ribbon tension is released and the ultrasonic cannulation assembly 48 may be easily moved from side to side or rotated at a slight angle until the optimum ultrasound image is obtained, at which juncture the gripping elements are re-engaged with adhesive ribbon 42 to secure sensor assembly 10 in place.

Cover 30 bears transverse grid markings 32, longitudinal grid markings 34 and a notch-like needle guide 40, which are used in combination to help guide the needle towards the vessel to be accessed. The transverse grid markings 32 are aligned parallel to transverse transducer array 14 and centered with respect to the head of the "T," while the longitudinal grid markings 34 are aligned parallel to longitudinal transducer array 16 and over the body of the "T." The needle guide 40 is aligned longitudinally with the body of the "T" and is adjacent the head end thereof. The notch of the needle guide 40 is aligned with a like notch of the frame element 46 to allow clear passage of the needle to the skin tissue underlying sensor assembly 10 without perforation of elongated, flexible, protective, transparent sheath 44 and possible compromise of the sterile field. After the optimum ultrasound image of the vessel is obtained through manipulation of sensor assembly 10 secured to frame element 46 and within protective, transparent sheath 44 and the ultrasonic cannulation assembly 48 is secured to the patient as described above, a needle with catheter attached is inserted into the tissue at a location defined by the needle guide 40. The needle is then guided towards the target vessel location, which is visually ascertained in relation to transverse grid markings 32 comprising letters A through E and longitudinal grid markings 34 comprising numerals 1 through 5 as will be hereinafter described. The method of guiding the needle towards the vessel using transverse grid markings 32 and 34 will become more apparent in the discussion of FIG. 3 which follows.

FIG. 3 is a representation of a dual-panel ultrasound image 50 generated by the monitoring system used with ultrasonic cannulation assembly 48 in the method of the present invention for the cannulation of blood vessels. The dual-panel ultrasound image 50 includes a transverse image 51 and a longitudinal image 53 of the neck displayed simultaneously in substantially real time on a single screen using known split-screen or picture-in-picture technology. The transverse image 51 is obtained from the transverse transducer array 14 of the sensor assembly 10 of FIGS. 1A and 1B and comprises a transverse image of the internal jugular vein 56 and a transverse image of the adjacent carotid artery 58. Also shown is a transverse grid display 52 which corresponds to the transverse grid markings 32 (letters A through E) on cover 30 of FIG. 2. Stated another way, transverse grid markings 32 are keyed to transverse grid display 52. The transverse grid display 52 and the transverse grid markings 32 indicate the relative location of the needle insertion point to the vessel to be punctured. For example, a needle inserted through the needle guide 40 of FIG. 2 would enter the tissue at a location proximate C relative to sensor assembly 10 on the transverse grid markings 32. However, FIG. 3 shows that the cross-sectional image of the internal jugular vein 56 is approximately laterally between B and C and that the cross-sectional image of the carotid artery 58 corresponds almost directly to C of the cross-sectional grid display 52. Therefore, in order to avoid the carotid artery and access the internal jugular vein, the sensor assembly 10 would be moved laterally until internal jugular vein 56 is directly below C on cross-sectional grid display 52.

Similarly, the longitudinal image 53 is obtained from the longitudinal transducer array 16 of the sensor assembly 10 of FIGS. 1A and 1B and displays a longitudinal image of the internal jugular vein 56 and an image of the skin surface 64. If the carotid artery 58 is substantially directly below internal jugular vein 56, carotid artery 58 will also be shown, as depicted in FIG. 3. In addition, a needle image 66 may optionally be displayed to show the location of the needle tip 66T as it passes from the skin surface 64 through the tissue toward the longitudinal image of the internal jugular vein 56. Thus, the needle image 66 provides the clinician with a precise indication of impending needle entry through a vessel wall. The imaging method may be used with a needle designed to enhance the image of the needle tip by plating or otherwise treating the needle tip surface with a material that is highly reflective of ultrasonic waves, such needles being known in the art and being termed "echogenic." One such needle employs a tip dipped in a polymer including gas bubbles therein, providing a diffuse rather than specular reflection. Also shown is a longitudinal grid display 54 which corresponds to the longitudinal grid markings 34 on cover 30 of FIG. 2. Stated another way, longitudinal grid markings 34 are keyed to longitudinal grid display 54. The longitudinal grid display 54 and the longitudinal grid markings 34 indicate the relative longitudinal location of the needle to the target blood vessel as it passes through the tissue under sensor assembly 10 in a manner analogous to the example above for the transverse grid display 52 and the transverse grid markings 32.

FIG. 3 also includes an example of how blood flow information is indicated to the user of the preferred embodiment of the present invention. As discussed above, the Doppler transducer element 18 of FIGS. 1A and 1B provides blood flow information to help distinguish veins from arteries within a patient's body. In FIG. 3, blood flow direction indicators 68 and 70 represent a means of providing visually perceptible indicia to identify blood flow direction in correspondence with longitudinal image 53. In the embodiment of FIGS. 1A and 1B, a single scan line of Doppler information obtained from the Doppler transducer element 18 is overlaid on top of the longitudinal image 53. The preferred method of distinguishing blood flow direction between two potential target vessels, one direction of blood flow depicted by indicator 68 and blood flow in the opposite direction depicted by indicator 70, is to display indicators 68 and 70 in two distinctly different colors. For example, a color coding scheme may be defined such that deoxygenated blood flow in veins corresponds to the color blue and oxygenated blood flow in arteries corresponds to the color red. Thus, blood flowing towards the heart in the longitudinal image of the internal jugular vein 56 could be indicated by displaying indicator 68 in blue while blood flowing towards the head in the longitudinal image of the carotid artery 58 could be indicated by displaying indicator 70 in red. This color coding scheme is also carried over to the orientation markings 36 and 38 on cover 30 of FIG. 2. Thus, in the present example, orientation marking 36 would be blue to further indicate blood flowing towards the heart and orientation marking 38 would be red to further indicate blood flowing towards the head. The inventors recognize that any combination of colors, including variations in gray-scale shading, may be used to indicate blood flow direction and such variations are encompassed by the present invention. Further, it is recognized that many other methods of indicating blood flow direction may be used including, but not limited to, displaying on image 51 or image 53 symbols, patterns, letters, or words corresponding to distinct blood flow directions. Also, blood flow direction may be indicated for the sake of simplicity by displaying only one indicator corresponding to either blood flow towards or away from the heart. Blood flow velocity may also be calculated from the signals sent and received by Doppler transducer element 18.

Figure 4:
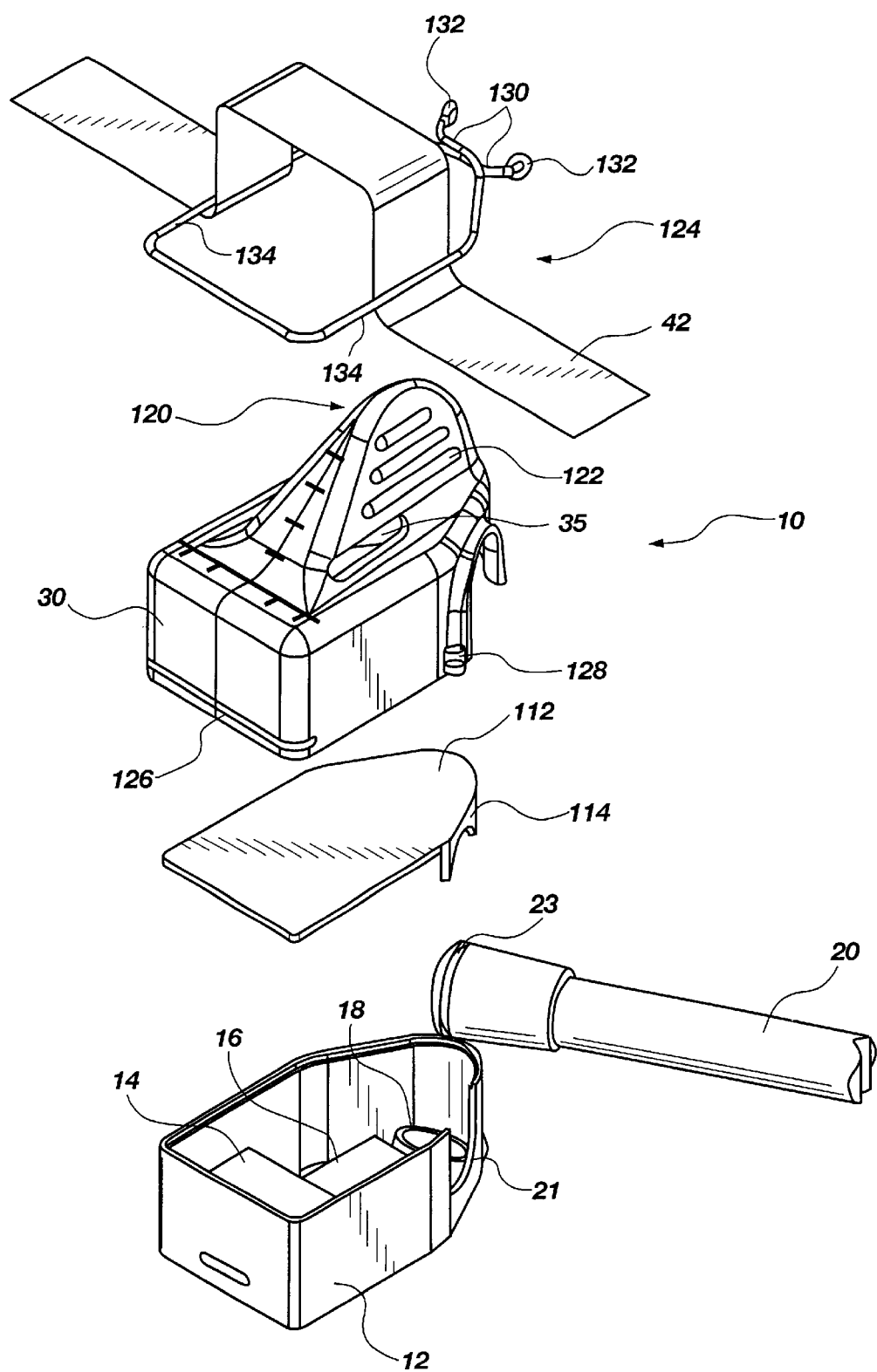
FIG. 4 comprises an exploded, detailed view of one exemplary implementation of a sensor assembly of the present invention employed in combination with a ribbon-type reference location element.

FIG. 4 depicts a more detailed implementation of the sensor assembly 10 depicted in FIGS. 1A, 1B and 2. Elements and features previously identified with respect to FIG. 2 are identified by the same reference numerals in FIG. 4. Linear transducer arrays 14 and 16 and Doppler transducer element 18 are shown disposed in housing 12, multi-conductor cable 20 entering housing 12 through a cutout 21 in the side wall thereof. An array housing lid 112 having protrusion 114 secures the end of multi-conductor cable 20 in cooperation with cutout 21, the side wall of the housing 12 and the protrusion 114 gripping multi-conductor cable 20 in annular slot 23. Cover 30, also termed a "shell," is configured to conformally extend over housing 12 and the bottom end thereof is configured to engage frame element 46 (not shown in FIG. 4) in a snap-fit fashion, housing 12 being trapped therebetween. Riser 120 extends upwardly from the main body of cover 30 and includes a plurality of gripping elements 122 on each side thereof to assist gripping of riser 120 by the fingers of the clinician. Slots 35 extend through each side of riser 120, and adhesive ribbon 42 (shown above cover 30 in FIG. 4 for clarity) extends through slots 35 and to either side of cover 30. A resilient gripping element in the form of spring clip 124 extends about the lower periphery of cover 30 in engagement with slots 126 and 128, the crossed ends 130 of spring clip 124 having loops 132. When in a relaxed position, the side rails 134 of spring clip 124 snugly clamp adhesive ribbon 42 against the side walls of cover 30. However, when loops 132 are pressed toward each other, as by using the thumb and forefinger, side rails 134 are pushed away from the side walls of cover 30, permitting sensor assembly 10 to be slid back and forth and rotated somewhat with respect to adhesive ribbon 42, the latter due to a slot elongation greater than the width of the adhesive ribbon 42.

Figure 5:
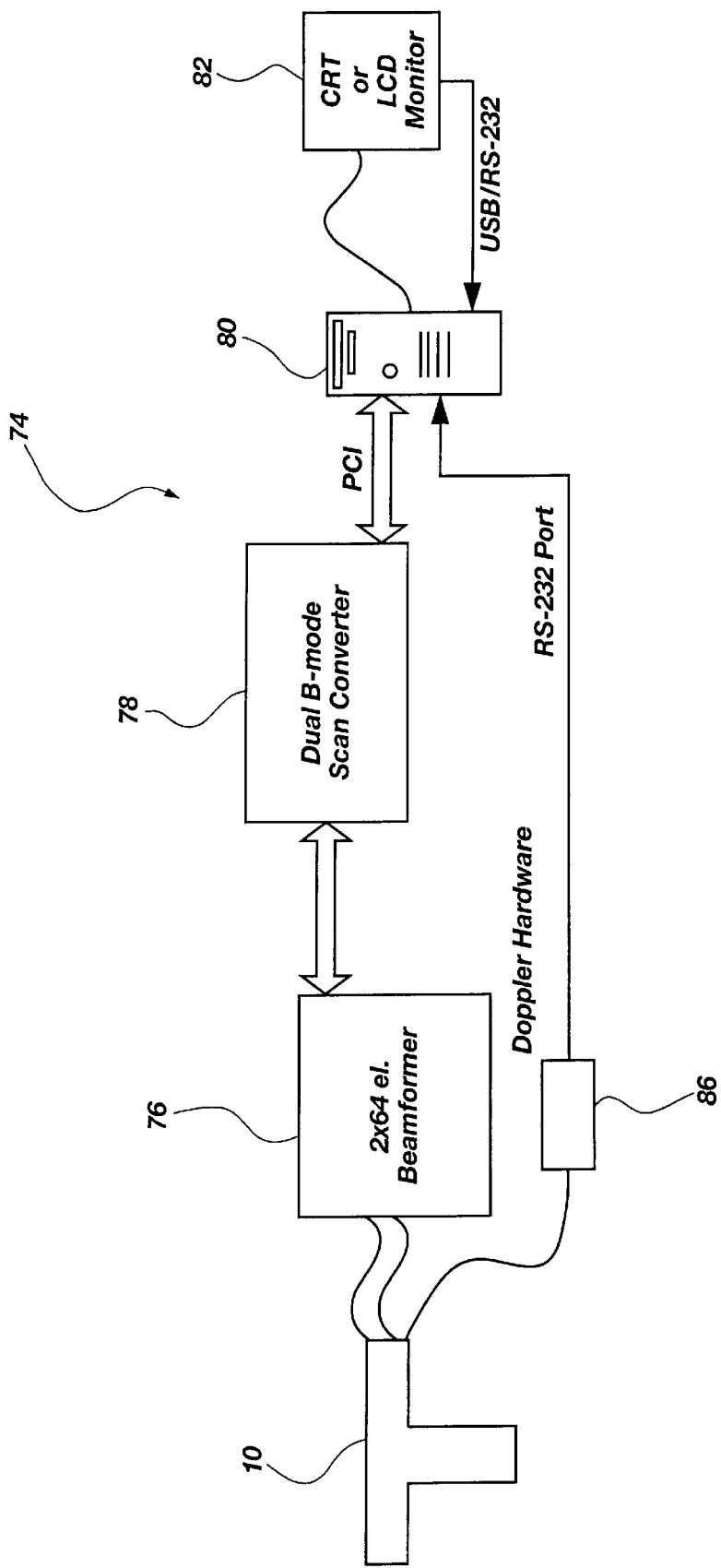
FIG. 5 is a block diagram of an exemplary system for the cannulation of blood vessels incorporating a sensor assembly of the present invention.

As shown in FIG. 5, a monitoring system 74 includes a multi-element ultrasonic beamformer (also termed "processing board") 76 and Doppler hardware 86 (see FIGS. 6 and 7) of sensor assembly 10 operably coupled to the multi-conductor cable 20 of the sensor assembly 10 of FIGS. 1A and 1B. Further, the monitoring system 74 includes a dual B-mode digital scan converter 78 coupled to the beamformer 76, a suitably programmed host computer 80 such as a personal computer, and a display device 82, which may comprise a cathode ray tube (CRT) monitor. Other types of monitors such as LCD touch screen monitors, or TFT monitors, may also be employed. Suitable beamformers and scan converter boards are available, for example, from B-K Medical of Copenhagen, Denmark, Analogic, Inc. of Peabody, Mass. and Telemed of Vilnius, Lithuania.

By way of further exemplary detail, the housing 12 may define dimensions of (L×W×H) of 42 mm×21 mm×11 mm. A Zero Insertion Force (ZIF) connector is used to connect transducer arrays 14 and 16 to Doppler transducer element 18. Multi-conductor cable 20 comprises a one centimeter diameter cable which exits the side of the housing 12. The elongated transducer arrays 14 and 16 each comprise piezoelectric arrays including sixty-four elements with an element pitch of 0.3 mm which operate at 7.5 MHZ. Focal depth is 20 mm (although a variety of focal lengths may be provided) and the elements possess about a 50–60% 6 dB bandwidth. Doppler transducer element 18 is also piezoelectric, includes a piezoelectric transmitter Tx and a piezoelectric receiver Rx and operates at 5 MHZ, possessing greater than a 75% 6 dB bandwidth. A single piezoelectric element performing as both a transmitter and receiver may also be used. The diameter of the combined transmitter and receiver is 8 mm, and the focal depth is 20 mm (although, again, a variety of focal lengths may be provided). Doppler transducer element 18 is oriented in housing 12 such that incident angle $\phi$ of beam 22 is 30°.

The dual B-mode digital scan converter 78 takes image information from the beamformer 76 via a 34-pin ribbon cable and displays the information on display device 82 in substantially real time. By "substantially" real time it is meant that image data from one array will be interleaved by host computer 80 with data from the other array and displayed simultaneously in a dual-panel, split-image format at 10–20 frames per second per image.

The host computer 80 may comprise a specifically packaged personal computer having the ability to run a Microsoft Windows operating system as well as appropriate ultrasound imaging software. The software is preferably stored on a solid-state drive (Disk on Chip) as opposed to a conventional disc drive, in order to facilitate the boot-up and boot-down processes. It is currently believed that the minimum hardware requirements for host computer 80 include a Pentium 133 MHZ or better processor, 32 MB of DRAM, 128 MB hard disk capacity, one RS-232 port, PCI Bus interface ports and a compatible video card, many of which are commercially available from multiple sources.

Figure 6:
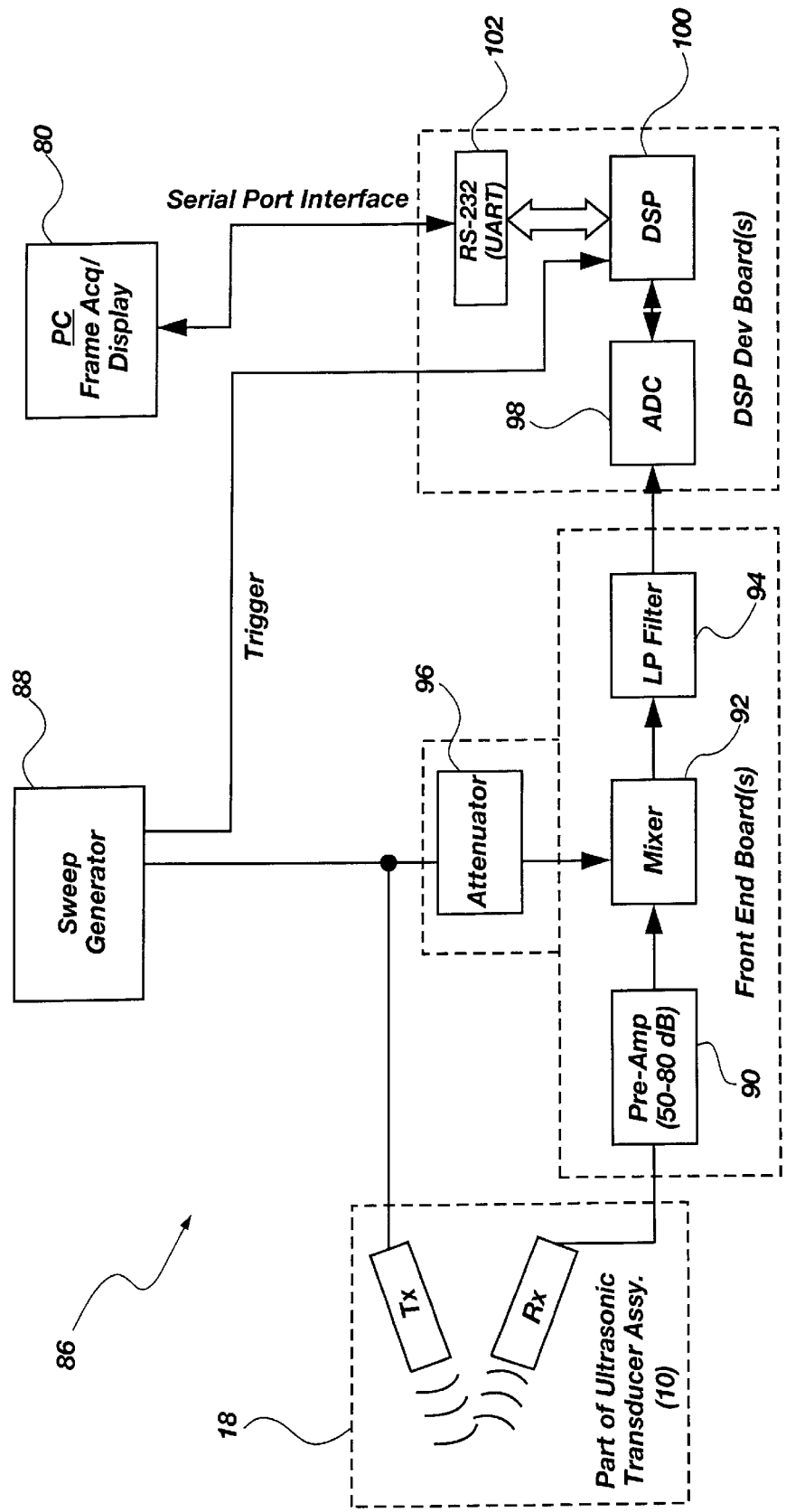
FIG. 6 is a block diagram of one embodiment of exemplary Doppler processing hardware for "chirped" Doppler suitable for use in the system of FIG. 5.

As shown in FIG. 6, chirped Doppler hardware 86, if used in the system of FIG. 5, includes a pre-amplifier 90 coupled to the Doppler transducer element 18 of FIGS. 1A and 1B, a mixer 92, a low-pass filter 94, an analog-to-digital converter 98 ("ADC"), a digital signal processor 100 ("DSP"), a serial communication device 102 for interfacing the DSP 100 to the host computer 80 of FIG. 5, a sweep generator 88 coupled to the Doppler transducer element 18 of FIGS. 1A and 1B and an attenuator 96. The Doppler transducer element 18 may, as previously noted, employ chirped Doppler to convert depth information into the frequency domain, allowing the user to obtain Doppler information at discrete depths which correspond to discrete frequency "bins." Alternatively, a conventional pulsed Doppler technique may also be employed. Data gathered by Doppler transducer element 18 is coded into a bit vector and sent over an RS-232 port to host computer 80 where the bit vector is converted to a color vector indicative of blood flow direction which is overlaid on top of longitudinal image 53 generated by dual B-mode digital scan converter 78.

Figure 7A:
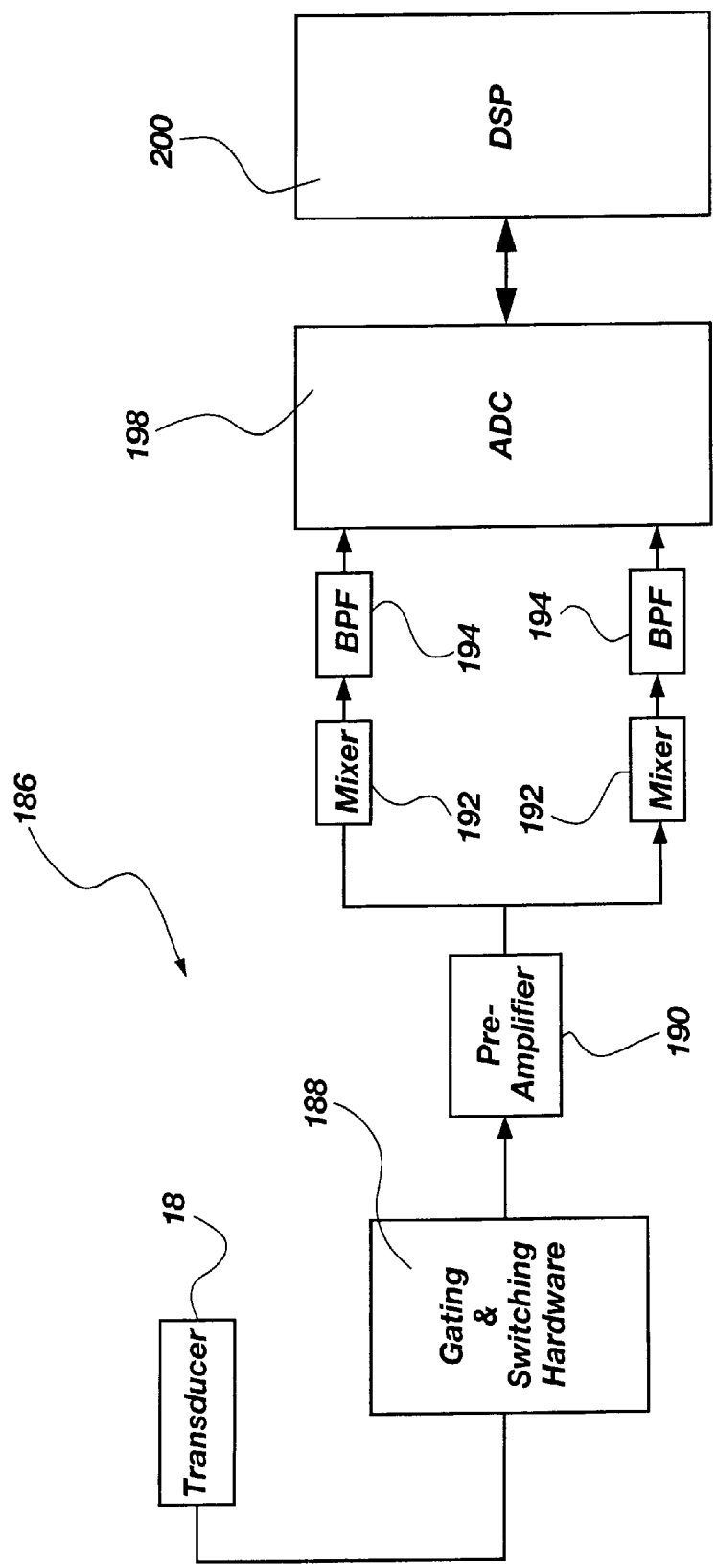
FIG. 7A is a block diagram of another embodiment of exemplary Doppler processing hardware for a first approach to "pulsed" Doppler suitable for use in the system of FIG. 5.

As shown in FIG. 7A, one embodiment of pulsed Doppler hardware 186, if used in the system of FIG. 5, includes gating and switching hardware 188 coupled to the Doppler transducer element 18 of FIGS. 1A and 1B and to a pre-amplifier 190 which, in turn, is coupled to dual mixers 192, each of which are coupled to band pass filters ("BPF") 194, these being coupled to an analog-to-digital converter 198 ("ADC"), a digital signal processor 200 ("DSP") and a serial communication device 102 (see FIG. 6) for interfacing the DSP 200 to the host computer 80 of FIG. 5. The Doppler transducer element 18 may, as previously noted, employ pulsed Doppler to obtain Doppler information at discrete depths. Data gathered by pulsed Doppler transducer element 18 is coded into a bit vector and sent over an RS 232 port to host computer 80 where the bit vector is converted to a color vector indicative of blood flow direction which is overlaid on top of longitudinal image 53 generated by dual B-mode digital scan converter 78.

Figure 7B:
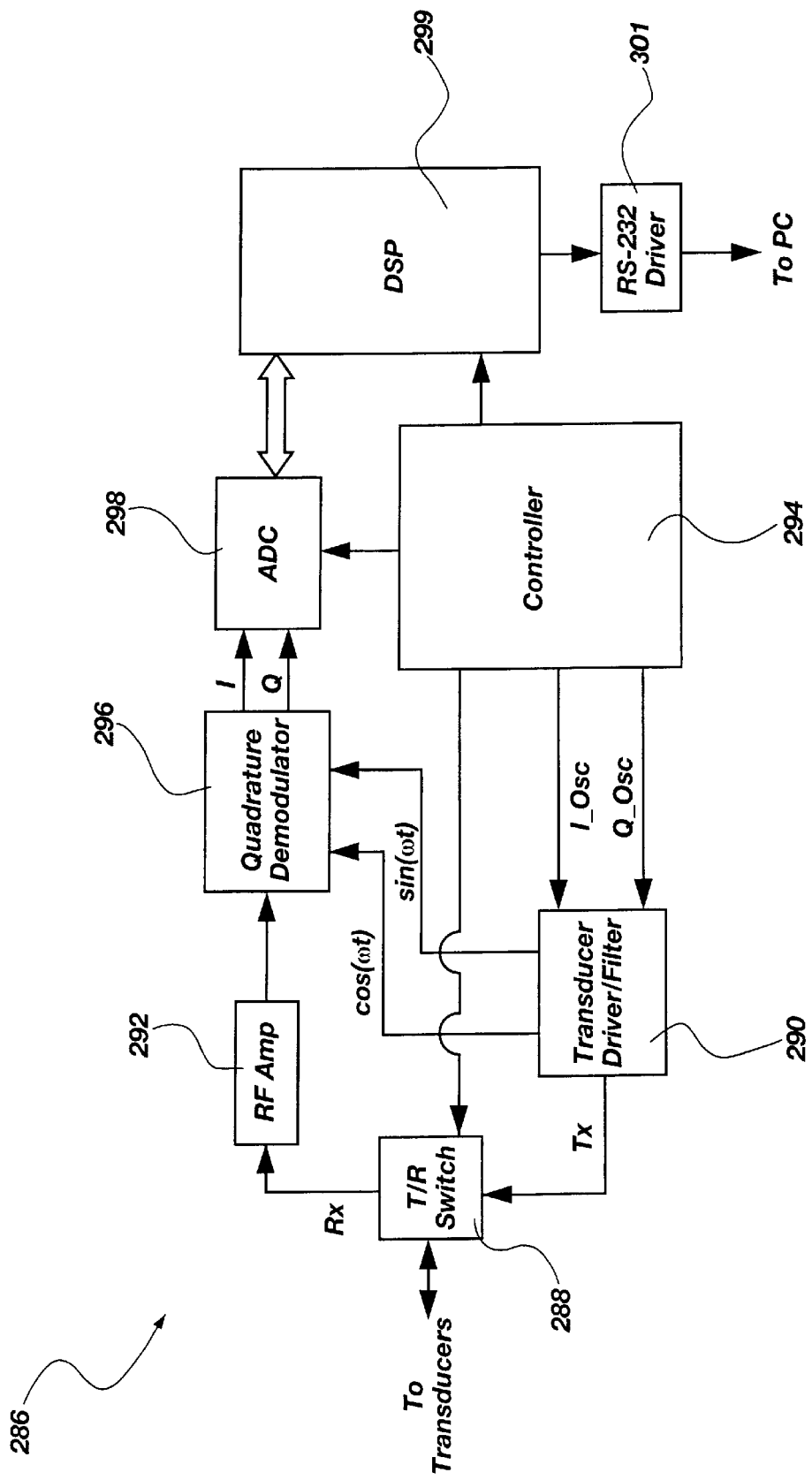
FIG. 7B is a block diagram of yet another embodiment of exemplary Doppler processing hardware for a second approach to "pulsed" Doppler suitable for use in the system of FIG. 5.

As shown in FIG. 7B, another embodiment of pulsed Doppler hardware 286, if used in the system of FIG. 5, includes transmit/receive switching hardware 288 coupled to two mutually separated groups of active imaging transducer elements of longitudinal transducer array 16 (see FIG. 7C), a transducer driver/filter 290 for transmitting pulsed signals and an RF amplifier 292 for receiving reflected pulsed signals. The transducer driver/filter 290 is coupled to and receives output from a controller 294 and to a quadrature demodulator 296, which receives output therefrom and which is also coupled to RF amplifier 292. Quadrature demodulator 296 is coupled and outputs to analog-to-digital converter ("ADC") 298, as does controller 294. ADC 298 outputs to digital signal processor ("DSP") 299. DSP 299 is coupled to and communicates with ADC 298. DSP 299 outputs to host computer 80 (see FIG. 5) through RS-232 driver 301. Data gathered by the two groups of active imaging elements acting as pulsed Doppler elements is manipulated as known in the art to provide blood flow direction and velocity data. The sign (positive or negative) of the output received from each channel, in association with relative magnitudes of the signals, is used to determine blood flow direction.

Figure 7C:
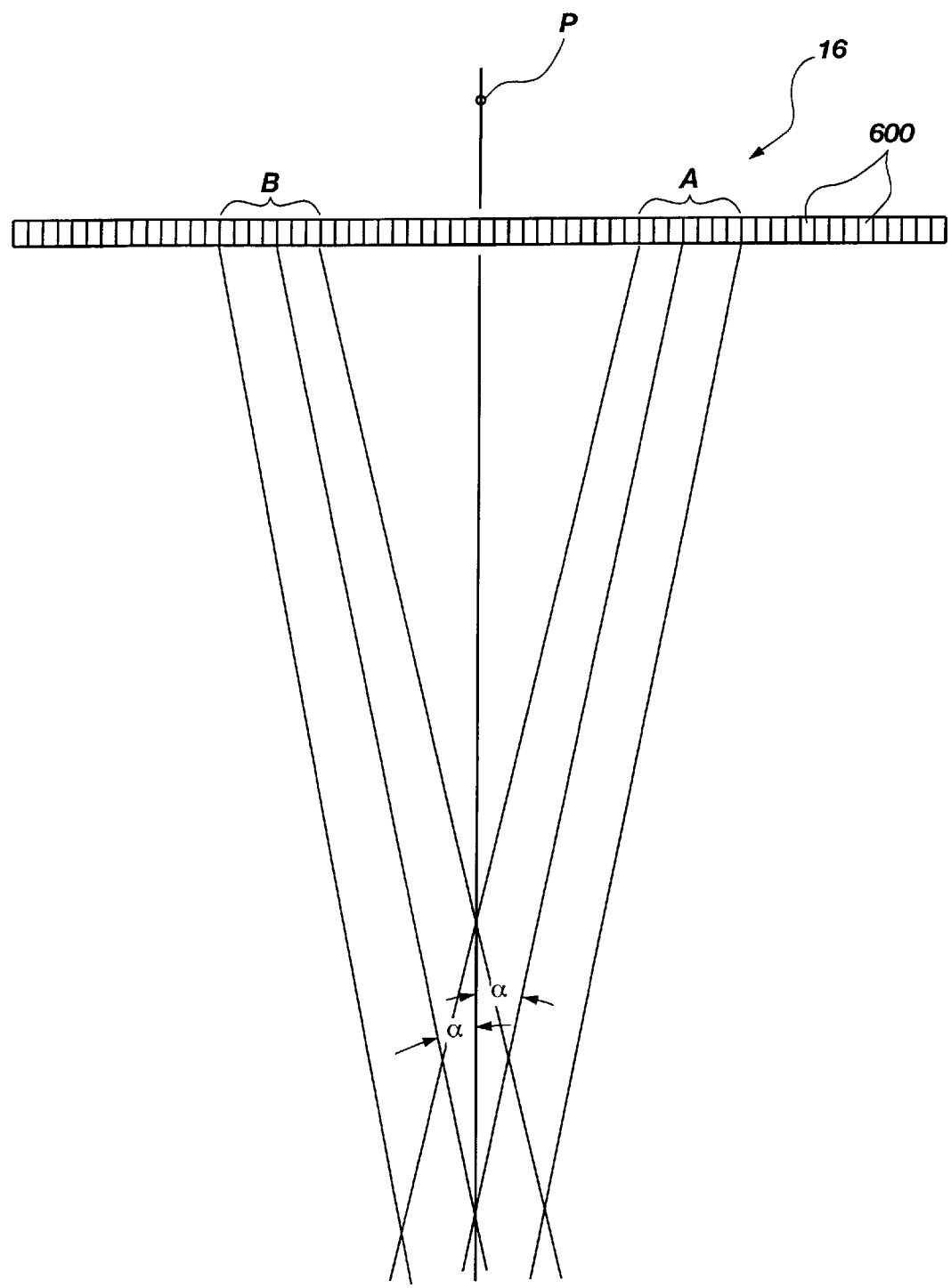
FIG. 7C is a schematic side elevation of a longitudinal imaging transducer array, wherein groups of active imaging transducer elements thereof are employed as Doppler elements in association with the components of FIG. 7B.

Referring to FIG. 7C, longitudinal transducer array 16 suitable for use with pulsed Doppler hardware 286 comprises a plurality of piezoelectric active imaging elements 600, for example, sixty-four elements of 0.3 mm length each, forming an array of 19.2 mm length. FIG. 7C is greatly enlarged for clarity. Two groups A and B of elements 600, for example, seven elements 600 per group along a distance of 2.1 mm, are separated along the length of transducer array 16 of, for example, 6.9 mm. Each group of elements 600 is employed as a pulsed Doppler element configured to emit and receive ultrasound signals at the same but opposing angle α, which may also be termed a "steering angle," to a perpendicular P to the plane of transducer array 16 in association with the hardware described above with respect to FIG. 7B. Angle α may comprise a relatively small angle, for example 12.2°. It should be noted that this implementation of the present invention may be fabricated in a more compact form than those employing a separate Doppler element placed at the end of transducer array 16, being as much as about 25% longitudinally shorter. Thus, for individuals having short necks, and especially children and infants, this implementation may provide significant advantages with respect to ease of placement and use.

Referring now to FIGS. 8A through 8D and 9A through 9D, another exemplary implementation of the sensor assembly 10 of the present invention is employed in combination with a magnetic reference location element 300 to form, in combination, an ultrasonic cannulation assembly of the present invention. In this variation, the elements of sensor assembly 10 are as previously described, with the exception of some aspects of cover 230. Elements and features previously described herein are identified by the same reference numerals in FIGS. 8A through 8D. Cover 230 is sized to conformally fit over housing 12 (not shown) which has been snapped into frame element 46 (see FIG. 4) associated with elongated, flexible, protective, transparent sheath 44 as previously described. Housing 12, which is placed inside elongated, flexible, protective, transparent sheath 44 over a mass of acoustic transmission gel is snapped into frame element 46, which is placed opposite the bottom of housing 12 on the outside of sheath 44. Cover 230 is then placed over housing 12 from the outside of the sheath 44 and snap-fit to frame element 46. Cover 230 includes wings 240 extending laterally from opposing sides thereof, each wing 240 carrying a magnet 242 disposed and secured in a downwardly facing cavity 244 thereof. It is currently preferred to use Neodymium magnets, offered by Jobmaster Magnets of Randallstown, Md. Wings 240 are preferably formed as integral portions of cover 230, curve arcuately away from the sides of cover 230 (see FIG. 8B) and are sized in length and cross-section to permit upward and downward flexing (see arrows) to accommodate different neck circumferences. Gripping elements 246, to facilitate gripping by the hands of the clinician for manipulation of sensor assembly 10, are located on each side of cover 230. In this embodiment, arrows on the top of cover 230 (see FIG. 8A), which may be respectively colored red (for arterial flow) and blue (for venous flow), indicate direction and type of blood flow. Cover 230 also includes a vertical slit 250 (see FIG. 8B) which facilitates ejection of sensor assembly 10 therefrom after use and defines a notch comprising needle guide 40 which, when assembled with frame element 46, is coincident with a notch formed therein. Arrows on the end of cover 230 (see FIG. 8B) point toward needle guide 40.

As shown in FIGS. 9A through 9D, reference location element 300 comprises a film or tape 302 having an adhesive 304 thereon, adhesive 304 being covered by tape backing 306 which includes folded portion 306a to facilitate gripping thereof when it is desired to remove backing 306 for application of film or tape 302 to the neck or location on the body of a patient. Film or tape 302 comprises a sandwich or laminate of two individual films coated on their facing surfaces with an adhesive, within which sandwich or laminate are disposed two metal discs or flexible polymer elements 310 of a magnetically sensitive or responsive material such as zinc-plated steel shim stock, metal discs or flexible polymer elements 310 being symmetrically located on each side of centerline CL of reference location element 300. Recess or cutout 312 at the periphery of film 302, which will be oriented toward the patient's head in use, facilitates needle insertion without having to penetrate film 302.

Of course, magnets 242 may be placed on reference location element 300, while metal discs 310 may be placed on cover 230, such arrangement being encompassed by the present invention. Furthermore, a magnetic tape comprising the aforementioned flexible polymer and in the form of an anisotropic conductive film, such as is used in refrigerator magnets, may be used in lieu of discrete magnets.

In use, the sensor assembly 10, secured within elongated, flexible, protective, transparent sheath 44 and having cover 230 placed thereover is placed over reference location element 300, which has been adhered to the patient by pulling backing 306 off of adhesive 304 and applying film 302 to the patient, adhesive-side down. An acoustic transmission gel has been placed over the outer surface of film 302, and sensor assembly 10 is placed over reference location element 300 with each of magnets 242 at least partially superimposed over one metal disc or polymer element 310, which is sized in diameter slightly larger than magnets 242. Due to the magnetic attraction between magnets 242 and metal discs or polymer elements 310, sensor assembly 10 is held firmly in place. However, the magnetic attraction is limited so that sensor assembly 10 may be moved laterally or vertically over reference location element 300 to position it precisely as previously described and for the purposes previously indicated.

It is also contemplated that other approaches for locating a sensor assembly on the patient are possible and encompassed by the present invention. For example, hook and loop fabrics such as those offered by Velcro Corporation may be employed. In one configuration, a collar for placement about the neck of a patient may be fabricated using, for example, a loop fabric on the exterior thereof and the sensor assembly may be provided with one or more patches of hook fabric for engaging the loop fabric of the collar to place, adjust and secure the sensor assembly to the collar. Alternatively, discs of loop fabric may be adhered to the skin of the patient and patches of hook fabric placed on the sensor assembly to place, adjust and secure the sensor assembly to the discs.

Further, while the present invention has been discussed for the sake of convenience in relation to cannulation of blood vessels, it is contemplated to have equal utility in placement of nerve blocks. For example, if it is desired to block the brachial plexus (a network of nerves formed by spinal nerves C5 to C8 and T1 with contributions from C4 and T2, which constitutes the entire nerve supply for the upper extremities, as well as a number of neck and shoulder muscles), the sensor assembly of the present invention may be used to visualize the adjacent artery and vein and to avoid the artery, vein and nerve bundle while placing the needle tip next to the nerve to initiate the block. Thus, the scope of the present invention encompasses the location of blood vessels for reference and locational purposes, regardless of whether the blood vessels or some other structure inside the body is of interest as a target location.

Figure 10A:
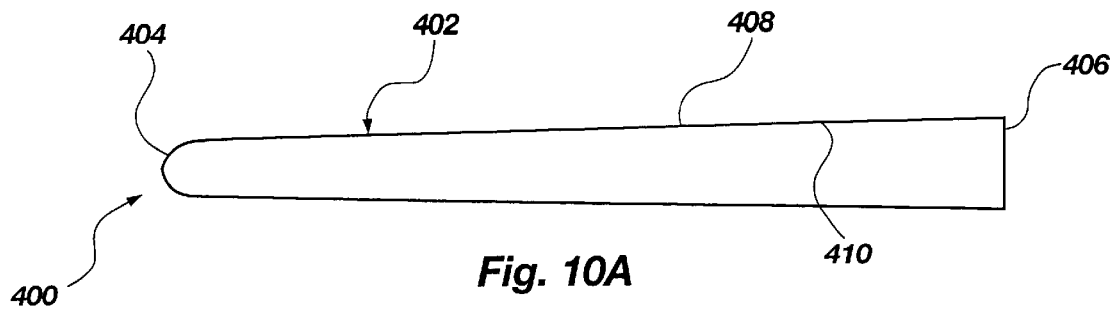
FIGS. 10A through 10D schematically depict a protective sheath and manipulation thereof for packaging and use, according to the present invention.
Figure 10B:
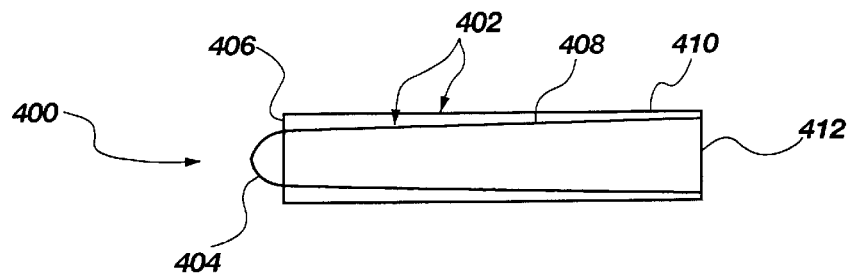
Figure 10C:
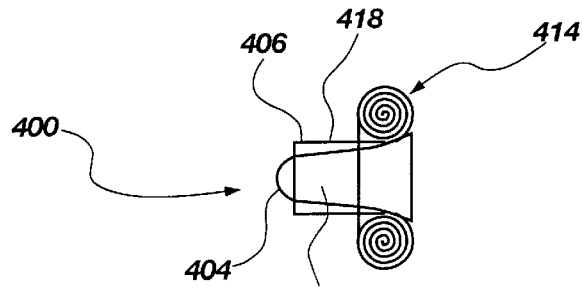
Figure 10D:
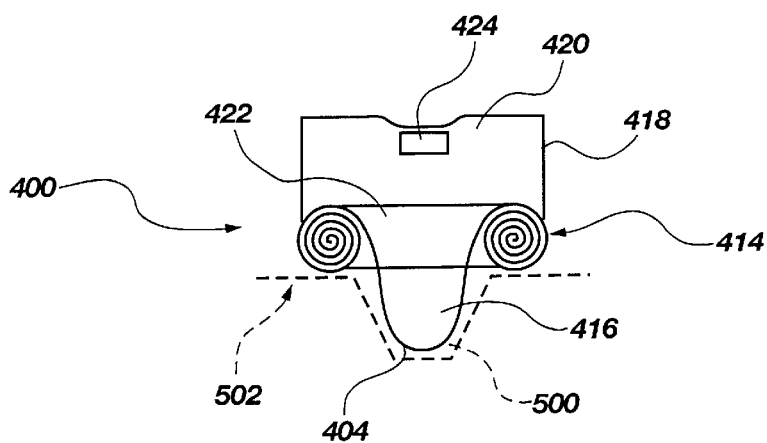

Referring now to FIGS. 10A through 10D of the drawings, an inventive embodiment of elongated, flexible, transparent protective sheath 44 is depicted. As shown in FIG. 10A, inventive sheath 400 may comprise a low-density polyethylene polymer film defining a substantially tubular body 402 and having a closed end 404 and a first open end 406. If desired, tubular body 402 of sheath 400 may taper from a relatively smaller cross-section proximate closed end 404 to a relatively larger first open end 406, but this is not required. In preparation for ultimate use and for packaging, tubular body 402 is everted, or turned inside-out, by drawing first open end 406 back over the exterior surface 408 thereof until everted first open end 406 lies proximate the closed end 404 as shown in FIG. 10B so that a portion of the former interior surface 410 of sheath 400 now lies on the exterior thereof and a second open end 412 is created at the opposite end of everted sheath 400 from closed end 404 and first open end 406. The polymer film at second open end 412 is then rolled outwardly over the doubled polymer film to form a toroidal shape 414 of rolled, doubled polymer film until a location proximate the closed end 404 is reached, leaving a pouch 416 surrounded by a skirt 418 of polymer film comprising everted first open end 406, as shown in FIG. 10C. Skirt 418 is then folded back over the toroidal shape 414 of rolled, doubled polymer film, the resulting structure being shown in FIG. 10D. As also shown in FIG. 10D, the resulting structure may be placed in a cavity 500 in a tray 502 with the upper mouth 420 of the folded-back skirt 418 facing upwardly, as is the lower mouth 422 of toroidal shape 414 of rolled, doubled polymer film opening into pouch 416. The tray 500, with sheath 400, frame element 46, cover 230, reference location element 300, sterile acoustic transmission gel, cotton gauze pads, cotton swabs, user guide and cautionary statement, is then packaged and sterilized, as known in the art. At the surgical theatre or other location of use, a sensor assembly 10 may be easily inserted into sterile pouch 416 by an individual after disposition of acoustic transmission gel therein as previously discussed, after which another individual may grasp the lower mouth 422 of folded-back skirt 418 proximal to upper mouth 420 and pull sheath 400 back to extend it along and over multi-conductor cable 20, the sterility of the exterior of sheath 400 thus being maintained free from potential contamination by the nonsterile sensor assembly 10 and multi-conductor cable 20 on the interior thereof. The extension of the sheath 400 may be facilitated by affixing two tabs 424 of, for example, paper, cardboard or a polymer proximate the edge of folded-back skirt 418, the tabs being affixed at opposite sides of the edge of folded-back skirt 418. The tabs 424, which may be brightly colored to aid visibility, aid the individual who grasps and extends the sheath 400 by providing an easily seen visual landmark or reference point on an otherwise transparent and featureless edge of folded-back skirt 418. It is envisioned that the individual who extends sheath 400 may place the thumb and forefinger of each hand, respectively, on a pull tab 424, grasping the pull tabs 424 adjacent the edge of folded-back skirt 418 and gently pulling in order to extend sheath 400. Sterile frame element 46 and cover 230 may then be assembled with housing 12 of sensor assembly 10 and a procedure performed, as previously described. Of course, the protective sheath 400 is not limited to use with the inventive sensor assembly 10 of the present invention, but may be employed with any sensor introducible thereinto.

Although the present invention has been described with reference to particular embodiments, the invention is not limited to these described embodiments. Rather, the invention is limited only by the appended claims, which include within their scope all equivalent devices or methods that operate according to the principles of the invention as described.

What is claimed is:

1. A system for use in cannulation of blood vessels in a body portion of a mammal, comprising:
- a sensor assembly including two linear, mutually perpendicular ultrasonic transducers, each comprising at least one element and at least one ultrasonic Doppler transducer element, the sensor assembly being configured for placement on the body portion with transducer elements of the sensor assembly aimed thereat;
- a beamformer operably coupled to the two linear, mutually perpendicular ultrasonic transducers and the at least one ultrasonic Doppler transducer element;
- a dual B-mode digital scan converter operably coupled to the beamformer for converting signals therefrom to images respectively depicting a transverse sectional view of blood vessels in the body portion and a longitudinal sectional view of the blood vessels in the body portion;
- Doppler signal processing hardware operably coupled to the at least one ultrasonic Doppler transducer element and configured to convert a Doppler signal received therefrom into a color image indicative of at least one direction of blood flow in at least one of the blood vessels of the body portion;
- a host computer operably coupled to the Doppler signal processing hardware and the dual B-mode digital scan converter; and
- a display device operably coupled to the host computer and configured to display the transverse sectional and longitudinal sectional views substantially simultaneously with the color image indicative of at least one direction of blood flow.

2. The system of claim 1, further comprising:
- an elongated, flexible, protective sheath having an open end and a closed end and having the sensor assembly received therein and secured to a frame element adjacent a surface thereof proximate the closed end;
- a cover located adjacent the frame element with the sensor assembly and a portion of the elongated, flexible, protective sheath disposed therebetween; and
- a reference location element configured to be secured to skin of a patient and for cooperative placement of the cover thereover for movable affixation of the sensor assembly thereto.

3. The system of claim 1, wherein the at least one ultrasonic Doppler transducer element comprises two ultrasonic Doppler transducer elements configured from one of the linear, mutually perpendicular ultrasonic transducers.

4. The system of claim 1, further comprising a grid system employed with the sensor assembly and which grid system the display device is configured to display in association with a position of the sensor assembly to coordinate positioning of the sensor assembly on the body portion.

5. The system of claim 1, wherein the two, linear, mutually perpendicular ultrasonic transducers comprise:
- a first linear, ultrasonic transducer array comprising a plurality of elements; and
- a second linear, ultrasonic transducer array comprising a plurality of elements; and wherein the sensor assembly further includes:
  - a housing carrying the first and second linear, ultrasonic transducer arrays and the at least one ultrasonic Doppler transducer element.

6. The system of claim 1, wherein the first and second linear, ultrasonic transducer arrays lie in mutually parallel planes and the elements of each of the first and second linear, ultrasonic transducer arrays are aimed substantially perpendicular to the planes.

7. The system of claim 1, wherein the first and second linear, ultrasonic transducer arrays are arranged to form a "T" shape with the first linear, ultrasonic transducer array defining a body of the "T" and the second linear, ultrasonic transducer array defining a head of the "T."

8. The system of claim 7, wherein the first linear, ultrasonic transducer array and the second linear, ultrasonic transducer array are each operably coupled to a multiconductor cable extending laterally from the housing at an angle to the body of the "T."

9. The system of claim 7, further comprising an elongated, protective, flexible sheath open at one end thereof and a frame element proximate a surface of the elongated, protective, flexible sheath at another, closed end thereof and engaged with the housing.

10. The system of claim 9, further comprising a cover engaged with the frame element and the housing with a portion of the elongated, protective, flexible sheath being interposed between the housing and the cover.

11. The system of claim 10, wherein the cover defines a needle guide at one end thereof proximate the head of the "T."

12. The system of claim 11, wherein the needle guide comprises a notch in the one end of the cover.

13. The system of claim 10, further comprising markings on an exterior surface of the cover indicative of two opposing directions of blood flow parallel to the body of the "T."

14. The system of claim 10, further comprising a set of longitudinal grid markings parallel to the body of the "T" and a set of transverse grid markings parallel to the head of the "T" on an exterior surface of the cover.

15. The system of claim 14, further comprising markings on the exterior surface of the cover indicative of two opposing directions of blood flow parallel to the body of the "T."

16. The system of claim 10, further including a ribbon bearing adhesive at two spaced locations on a surface thereof flanking an adhesive-devoid location thereof extending through at least one slot in a structure associated with the cover.

17. The system of claim 16, wherein the cover further includes selectively engageable gripping elements for gripping the ribbon.

18. The system of claim 10, wherein the cover comprises a pair of wings laterally extending from opposing sides thereof, each wing carrying a magnet.

19. The system of claim 18, further including a reference location element for securing to skin of a patient over a target blood vessel, the reference location element comprising a film carrying two elements of magnetic material, spaced about a same distance as a distance between the magnets and each of a greater lateral dimension than one of the magnets, the film including an adhesive thereon for affixation to the patient's skin.

20. The system of claim 1, wherein the at least one ultrasonic Doppler transducer element is aligned with the first linear, ultrasonic transducer array, and carried by the housing.

21. The system of claim 20, wherein the at least one ultrasonic Doppler transducer element is adjacent an end of the first linear, ultrasonic transducer array.

22. The system of claim 21, wherein the at least one ultrasonic Doppler transducer element is aimed at an acute angle to a perpendicular to a plane of the first linear, ultrasonic transducer array.

23. The system of claim 22, wherein the acute angle is about 30° and the at least one ultrasonic Doppler transducer element is further aimed toward the first linear, ultrasonic transducer array.

24. The system of claim 20, wherein the at least one ultrasonic Doppler transducer element comprises two ultrasonic Doppler transducer elements, each comprising a group of elements from the first linear, ultrasonic transducer array, each group of elements being separated from the other along a length of the first linear, ultrasonic transducer array.

25. The system of claim 24, wherein each of the two ultrasonic Doppler transducer elements is aimed at the same but opposing acute angles to a perpendicular to a plane of the first linear, ultrasonic transducer array.

26. The system of claim 25, wherein the opposing acute angles are each about 12.2°.

27. The system of claim 26, wherein the elements of the first and second linear, ultrasonic transducer arrays each comprise a piezoelectric element.

28. The system of claim 20, wherein the elements of the first and second linear, ultrasonic transducer arrays and the at least one ultrasonic Doppler transducer element each comprise at least one piezoelectric element.

29. The system of claim 20, wherein the at least one ultrasonic Doppler transducer element is comprised of a piezoelectric transmitter and a piezoelectric receiver.

30. A method for the cannulation of a blood vessel, the method comprising:

obtaining and displaying a first ultrasound image of at least one blood vessel in a first imaging plane;

obtaining and displaying a second ultrasound image of the at least one blood vessel in a second imaging plane transverse to the first imaging plane;

obtaining Doppler information acquired at an angle incident to the second imaging plane and providing from the Doppler information a display of visually perceptible indicia indicative of blood flow direction in the at least one blood vessel;

viewing the displayed first and second ultrasound images of the at least one blood vessel and the display of visually perceptible indicia indicative of blood flow direction in the at least one blood vessel while guiding a needle having a catheter associated therewith to the at least one blood vessel; and penetrating the at least one blood vessel with the needle.

31. The method of claim 30, further comprising displaying the first ultrasound image, the second ultrasound image and the display of visually perceptible indicia indicative of blood flow direction in the at least one blood vessel substantially simultaneously on a single display device.

32. The method of claim 30, wherein obtaining Doppler information acquired at an angle incident to the second imaging plane and providing from the Doppler information a display of visually perceptible indicia indicative of blood flow direction in the at least one blood vessel comprises obtaining a single scan line of Doppler information, color coding the single scan line to be indicative of blood flow direction, and displaying the single scan line overlaid on top of the second ultrasound image.

33. The method of claim 32 wherein color coding the single scan line to be indicative of blood flow direction comprises color coding blood flowing in one direction blue and color coding blood flowing in an opposing direction red.

34. The method of claim 30, further comprising obtaining the first ultrasound image, the second ultrasound image and the Doppler information using a single sensor assembly temporarily attached to a surface of a patient's skin overlying the at least one blood vessel.

35. The method of claim 30, wherein obtaining the Doppler information comprises transmitting and receiving chirped ultrasound pulses to obtain Doppler information at discrete focal lengths.

36. The method of claim 30, wherein obtaining the Doppler information comprises transmitting and receiving ultrasound pulses to obtain Doppler information at discrete focal lengths.

* * * * *

UNITED STATES PATENT AND TRADEMARK OFFICE
CERTIFICATE OF CORRECTION

PATENT NO.       : 6,755,789 B2
APPLICATION NO. : 10/072662
DATED            : June 29, 2004
INVENTOR(S)      : Bradley J. Stringer et al.

It is certified that error appears in the above-identified patent and that said Letters Patent is hereby corrected as shown below:

On the title page:

Item (56) References Cited,
Other Publications, 2nd PAGE,
1st COLUMN, LINE 54,            change "Emboloism." " to --Embolism."-- and change "II," to --11,--

Item (56) References Cited,
Other Publications, 2nd PAGE,
2nd COLUMN, LINE 56,            change "Jan/Feb 6," to --6, Jan/Feb--

Item (56) References Cited,
Other Publications, 2nd PAGE,
2nd COLUMN, LINE 61,            change "Bolten," to --Bolton,--

Item (56) References Cited,
Other Publications, 3rd PAGE,
1st COLUMN, LINE 44,            change "Crossoverd" to --Crossover--

Item (56) References Cited,
Other Publications, 3rd PAGE,
2nd COLUMN, LINE 36,            change "Causred" to --Caused--

Item (56) References Cited,
Other Publications, 4th PAGE,
2nd COLUMN, LINE 13,            change "S.r." to --S.R.--

Item (56) References Cited,
Other Publications, 4th PAGE,
2nd COLUMN, LINE 37,            change "Critically III" to --Critically Ill--

Item (56) References Cited,
Other Publications, 4th PAGE,
2nd COLUMN, LINE 65,            change "Access vai" to --Access via--

Item (56) References Cited,
Other Publications, 5th PAGE,
2nd COLUMN, LINE 42,            change "Catheterization]/" " to --Catheterization]"--

UNITED STATES PATENT AND TRADEMARK OFFICE
CERTIFICATE OF CORRECTION

PATENT NO. : 6,755,789 B2
APPLICATION NO. : 10/072662
DATED : June 29, 2004
INVENTOR(S) : Bradley J. Stringer et al.

It is certified that error appears in the above-identified patent and that said Letters Patent is hereby corrected as shown below:

In the specification:
COLUMN 5, LINE 40, change "angle Φ," to --angle φ,--
COLUMN 6, LINE 10, change "angle Φ" to --angle φ--
COLUMN 10, LINE 51, change "angle Φ" to --angle φ--

In the claims:
CLAIM 6, COLUMN 16, LINE 1, change "claim 1," to --claim 5,--
CLAIM 7, COLUMN 16, LINE 6, change "claim 1," to --claim 5,--
CLAIM 20, COLUMN 16, LINE 59, change "claim 1," to --claim 5,--
CLAIM 20, COLUMN 16, LINE 61, change "array, and" to --array and--

Signed and Sealed this

Twenty-sixth Day of June, 2007

JON W. DUDAS
*Director of the United States Patent and Trademark Office*